United States Patent [19]

Feldon et al.

[11] Patent Number: 5,732,221

[45] Date of Patent: Mar. 24, 1998

[54] ELECTRONIC DOCUMENTATION SYSTEM FOR GENERATING WRITTEN REPORTS

[75] Inventors: Steven E. Feldon, San Marino; Jai P. Agrawal, Cypress, both of Calif.

[73] Assignee: Documation, Inc., Los Angeles, Calif.

[21] Appl. No.: 403,551

[22] Filed: Mar. 14, 1995

Related U.S. Application Data

[63] Continuation of Ser. No. 859,222, Mar. 27, 1992, abandoned.

[51] Int. Cl.⁶ .................................................. G06F 17/21
[52] U.S. Cl. ........................ 395/203; 395/768; 395/353
[58] Field of Search .............................. 395/155–161, 395/149, 203, 768, 352, 353; 345/173; 364/413.17, 413.22

[56] References Cited

U.S. PATENT DOCUMENTS

| | | | |
|---|---|---|---|
| Re. 34,476 | 12/1993 | Norwood | 345/173 |
| 3,794,982 | 2/1974 | McCormick et al. | 340/172.5 |
| 3,829,844 | 8/1974 | Zonneveld et al. | 340/172.5 |
| 4,007,443 | 2/1977 | Bromberg et al. | 340/172.5 |
| 4,053,951 | 10/1977 | Hudspeth et al. | 364/415 |
| 4,105,303 | 8/1978 | Guyton | 351/39 |
| 4,130,881 | 12/1978 | Haessler et al. | 364/900 |
| 4,216,462 | 8/1980 | McGrath et al. | 340/150 |
| 4,290,114 | 9/1981 | Sinay | 364/900 |
| 4,334,739 | 6/1982 | Seckinger | 351/39 |
| 4,375,671 | 3/1983 | Engle | 367/11 |
| 4,430,749 | 2/1984 | Schardt | 382/54 |
| 4,437,127 | 3/1984 | Hirose | 358/296 |
| 4,437,161 | 3/1984 | Anderson | 364/414 |
| 4,468,697 | 8/1984 | Verhoeven | 358/111 |
| 4,520,442 | 5/1985 | Grimberg et al. | 364/414 |
| 4,533,946 | 8/1985 | Yasuhara et al. | 358/111 |
| 4,611,247 | 9/1986 | Ishida et al. | 358/280 |
| 4,611,298 | 9/1986 | Shuldt | 364/900 |
| 4,654,818 | 3/1987 | Wetterau, Jr. | 364/900 |
| 4,789,235 | 12/1988 | Borah et al. | 351/246 |
| 5,049,862 | 9/1991 | Dao et al. | 340/706 |
| 5,220,675 | 6/1993 | Radawer et al. | 395/156 X |
| 5,241,655 | 8/1993 | Mineki et al. | 395/156 |

OTHER PUBLICATIONS

Venditto, "Pipeline: Tools for Pen–Based Computers Taking Shape," *PC Magazine* (Feb. 1991) pp. 67–69.

Venditto, "Pipeline: Techniques to Decipher Handwriting . . . Perfection in the Lab," *PC Magazine* (Sep. 1990) pp. 63–64.

O'Connor, "Go licenses software to IBM," *San Jose Mercury News*, Section F, Thursday morning, Jul. 19, 1990.

*Primary Examiner*—Mark K. Zimmerman
*Attorney, Agent, or Firm*—Townsend and Townsend and Crew LLP

[57] ABSTRACT

System and methods for generating written reports based on succinct input from a user. A method of the present invention comprises entering a first mode for initialization; defining menus; entering a second mode for receiving information; entering information using the defined menus; interpreting the entered information; and generating a written report in response to the interpreting step. A system (100) of the present invention comprises a portable computer system having a memory (102), a processor (101), a detachable keyboard (107), a screen (104), and a pen (105). Ancillary information is entered with the keyboard which is then detached. Subsequent information is documented by selecting appropriate items from the defined menus; alternatively, the information can be written on the screen with the pen. The processor is programmed to interpret the inputs and generate a report. The report may be printed on a printer (108), stored on a storage device, and/or transferred to another system.

11 Claims, 19 Drawing Sheets

Microfiche Appendix Included
(2 Microfiche, 164 Pages)

ELECTRONIC DOCUMENTATION SYSTEM FOR GENERATING WRITTEN REPORTS

This is a continuation of application Ser. No. 07/859,222, filed Mar. 27, 1992, now abandoned.

COPYRIGHT NOTICE

A portion of the disclosure of this patent document contains material which is subject to copyright protection. The copyright owner has no objection to the xerographic reproduction by anyone of the patent document or the patent disclosure in exactly the form it appears in the Patent and Trademark Office patent file or records, but otherwise reserves all copyright rights whatsoever.

MICROFICHE APPENDIX

A microfiche appendix (2 sheets, 160 frames) of a computer program listing for representative system software (©1992) is included herewith.

BACKGROUND OF THE INVENTION

The present invention relates generally to the use of computers in information processing and, more particularly, relates to automated methods for recording information and generating reports employing portable digital computers.

Documentation of information obtained from a variety of sources is becoming increasingly important due to emphasis on cost efficiency and competitiveness. It is known to use a computer system to automate the processing of information, for example, electronic spreadsheets, word processing, and databases. While these technologies have helped automate the collection and processing of information, they have been less successfully implemented in automating the chores of workers who typically report data on paper forms, such as delivery drivers, claims adjusters, and physicians.

Recently, portable systems have been introduced that can be held like a clipboard and recognize printed handwriting. One such system, the GridPad (Grid Systems Corporation, Fremont, Calif.) offers a modified IBM-compatible computer where commands are entered by touching designated spots on the systems LCD (liquid crystal display) screen with an electronic pen that is tethered to the machine. The GridPad uses neuro-network principles to recognize handwriting. Alternatively, numbers can be entered via a "pop-up" keyboard.

However, "pen-based" computers merely provide a means for electronically entering data typically recorded on paper forms. What is needed is a system which provides the advantages of pen-based systems and also provides complete, written reports from terse user input. The present invention fulfills this and other needs.

SUMMARY OF THE INVENTION

The present invention provides a system and methods for generating written reports based on succinct input from a user. This allows a user, for example, to document information by simply touching displayed data items on a screen with an electronic pen. From this user input, a complete written report is produced in full-text narrative form. The report can be printed out, stored on a storage device, and/or even transferred to a different system.

A method of the present invention comprises two modes of system operation. First, a mode for initialization, defining menus, and pull down keypads; and a second mode for receiving information, entering information using the defined menus, interpreting the entered information, and generating a written report in response to the interpreting step. For example, using the present invention, an examination of the eye is expedited by defining menus for the common types of eye exams. Then, a physician need only select the appropriate items on the menu (or enter additional information on a screen) to document the exam. From this input, the present invention generates a report documenting the exam. In a preferred embodiment, the report is a full text report written in English characterized by complete sentences with paragraph separation and appropriate punctuation (as opposed to a less discernible output typified by computers), the report being comprehensible by one without computer experience.

A system of the present invention comprises a portable computer system having a memory, a processor, a detachable keyboard, a screen, and a pen. Ancillary information is entered with the keyboard which is then detached. Subsequent information is documented by selecting appropriate items from the defined menus and pull down keypads; alternatively, the information is written on the screen with the pen. The processor is programmed to interpret the inputs and generate a report. A printer is provided for producing a hard copy of the report. The user may also store the report on a storage device and/or transfer the report to a remote system.

A further understanding of the nature and advantages of the inventions herein may be realized by reference to the remaining portions of the specification and the attached drawings.

DETAILED DESCRIPTION OF A PREFERRED EMBODIMENT

Table of Contents

I. Introduction
II. System Information
III. System Programming and Customization Mode
   A. System Menus and Menu Items
   B. Pull Down Keypads
IV. System Programming Mode: States of Operation
V. Eye Exam Documentation Mode
VI. System Software Requirements
VII. Function Control Software
   A. System Programming Mode Software
      1. Software for Programming the Exam Menus and Menu Items
      2. Software for Programming the Pull Down Keypads
      3. Software for Programming the Demographic Data Entry Forms
   B. Eye Exam Documentation Mode Software
      1. Software for Demographic Data Entry
      2. Software for the Selection and Documentation of Eye Exams
      3. Software for Exam Report Generation and Printout
      4. Software for Data Transfer Between Ocuchart and the Host Computer
   C. Internal Data Structures
      1. SPMR.DAT: System Parameters File
      2. MENU.DAT: Menu Data File
      3. ITEM.DAT: Menu Item Definition File
      4. KPD.DAT: Pull Down Keypad Definition File
      5. STR.DAT: Text String File
      6. DEF.DAT: Default Data File

I. Introduction

The following description is based on a specific embodiment of the invention adapted to operate on a GridPad portable computer running under a windowing environment. The system permits, among other things, the interactive manipulation of menu-presented information. Of course, this hardware configuration is merely for illustration. The invention may be embodied in other systems without departing from the scope of the invention.

Figure 1:
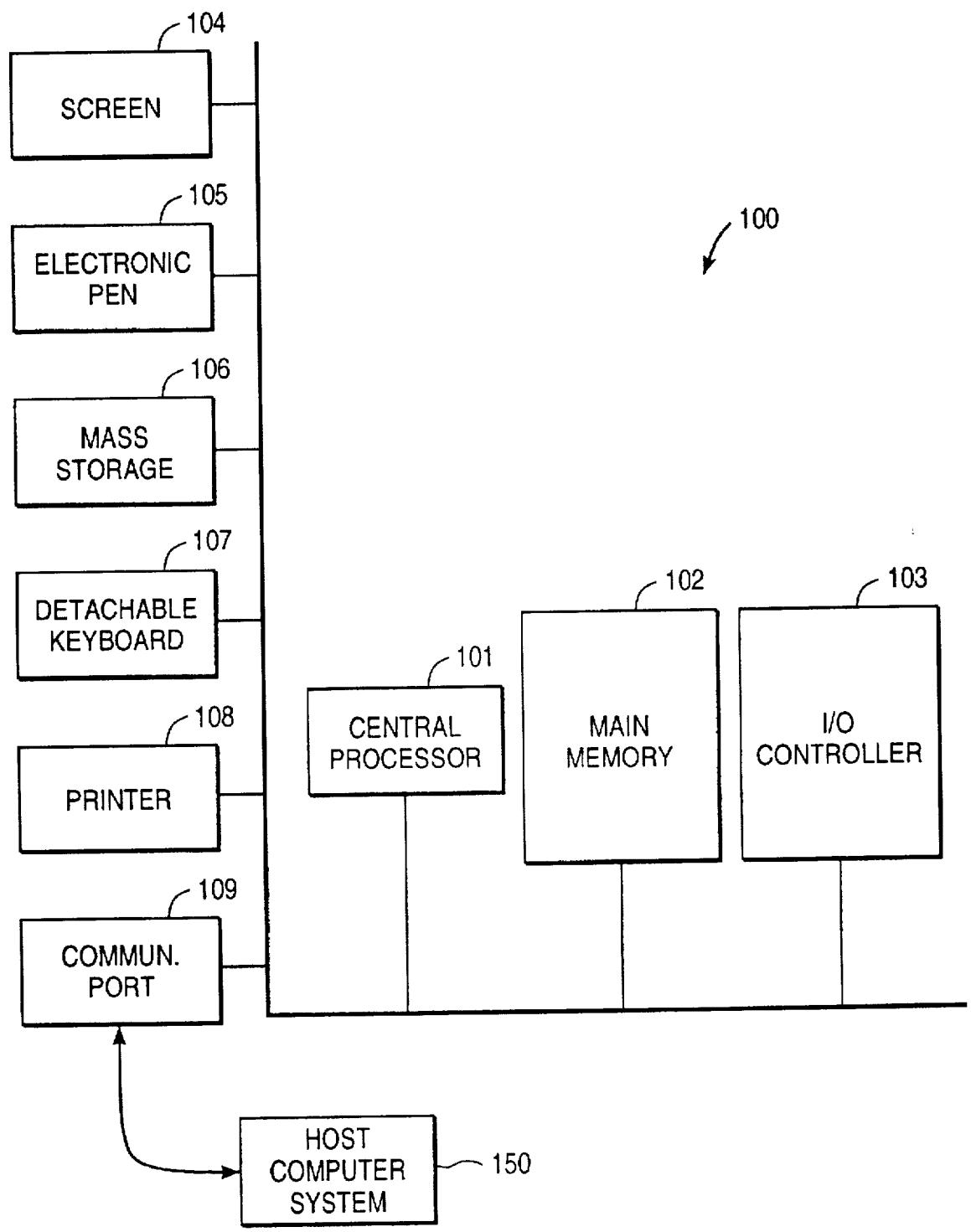
FIG. 1 is a block diagram of a computer system that the present invention may be embodied.

The present invention may be embodied in a pen-based computer system, such as the system 100 of FIG. 1, which comprises a central processor 101, a main memory 102, an I/O controller 103, a screen 104, an electronic pen 105, a mass storage 106, and a detachable keyboard 107. System 100 may be selectively coupled with a detachable keyboard 107 and a printer 108. A communication port 109, such as an RS-232 or SCSI (Small Computer System Interface) port, is provided for selective connection to additional peripherals or other computer systems, e.g., host computer system 150. The various components of system 100 communicate through a system bus 110. In a preferred embodiment, a GridPad portable computer (Grid Systems Corporation, Fremont, Calif.) running under MS-DOS is used.

System 100 employs built-in intelligent means to interpret succinct user-entered information and produce a complete, written report, for example, in plain English (as opposed to a less discernible output typified by computers). The report is a narrative text with complete sentences with paragraphs and appropriate punctuation. Appropriate title and headings are also included. Thus, the report is comprehensible by one without computer experience. This report can then be printed out to a hard copy or transferred to another computer system for further editing.

Screen 104 and pen 105 are used to enter information. The user selects a module for information to be documented by simply touching corresponding data items on screen 104. The data items are displayed in menu format; pop-up menus and keypads displayed on screen 104 when necessary for selecting and entering the desired information. Thus, using the electronic writing pad (screen 104 and pen 105) of system 100, information may be entered by drawing a pictorial view and/or by writing the text, thus doing away with the need for a keyboard. However, when appropriate, the user enters data and commands via detachable keyboard 107.

System 100 is programmable by the user to specify the menu data items for display in menu and submenu formats. It is also programmable by the user to specify the pull down keypads to be displayed corresponding to the selected menu items. Further, it is programmable by the user to enter the text (English or other desired language) associated with the displayed menu items. In response to user input, this text is incorporated when generating exam reports.

In a preferred embodiment of the invention, system 100 is adapted to documentation of an eye exam. Several data entry means are provided. This allows a physician, for example, to document the complete eye exam by simply touching the displayed data items on screen 104. Additional examination data may be entered by the user by drawing a pictorial view and/or by writing text using pen 105. Detachable keyboard 107 may be used, for example, to enter demographic information for each patient.

Preprogrammed data entry forms are provided for entering the patient's demographic information, medical history, prescribed medication, and other relevant information into system 100. However, the user is able to customize these data entry forms by editing the existing forms or by redesigning the completely new forms. For example, the data entry forms may be edited as desired, for the input and retrieval of a patient's demographic information.

II. System Information

Figure 2:
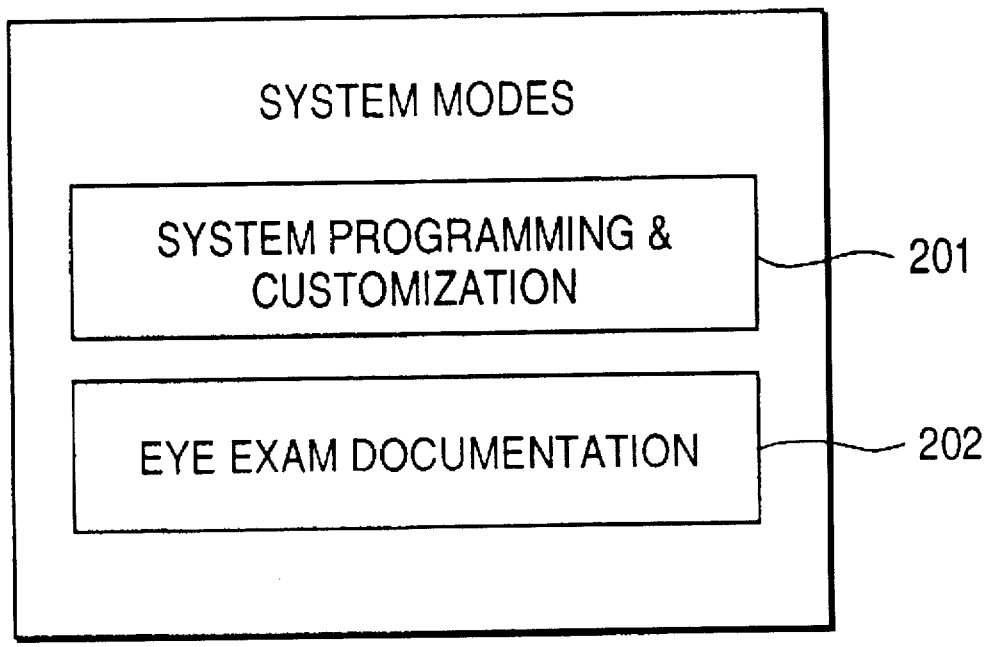
FIG. 2 is a block diagram of the system modes of operation.

Referring to FIG. 2, system 100 operates in two different modes: (1) System Programming and Customization Mode 201, and (2) Eye Exam Documentation Mode 202. In the former, the user is able to set up and customize the system (i.e., initialization). The latter mode is used to enter the patient's demographic information and the eye examination data to document and prepare the reports.

III. System Programming and Customization Mode

In this mode, the user defines the menus, menu items, text strings and default data strings (associated with the menu items), and the pull down keypads. In a preferred embodiment, these are pre-programmed for the most commonly performed eye examinations.

Since system 100 can be programmed according to the user's needs, it may be customized for the particular task at hand. Means are provided for editing existing information, as well as means for programming the system 100 for completely a new set of menus, submenus, data entry forms, and so forth. For example, the demographic and medical history data of the patient are part of the examination report. This information is entered into system 100 by the use of pre-programmed demographic data entry forms. However, the user is not restricted to the use of pre-programmed menus or data entry forms, but may customize these using keyboard 107.

A. System Menus and Menu Items

Figure 3:
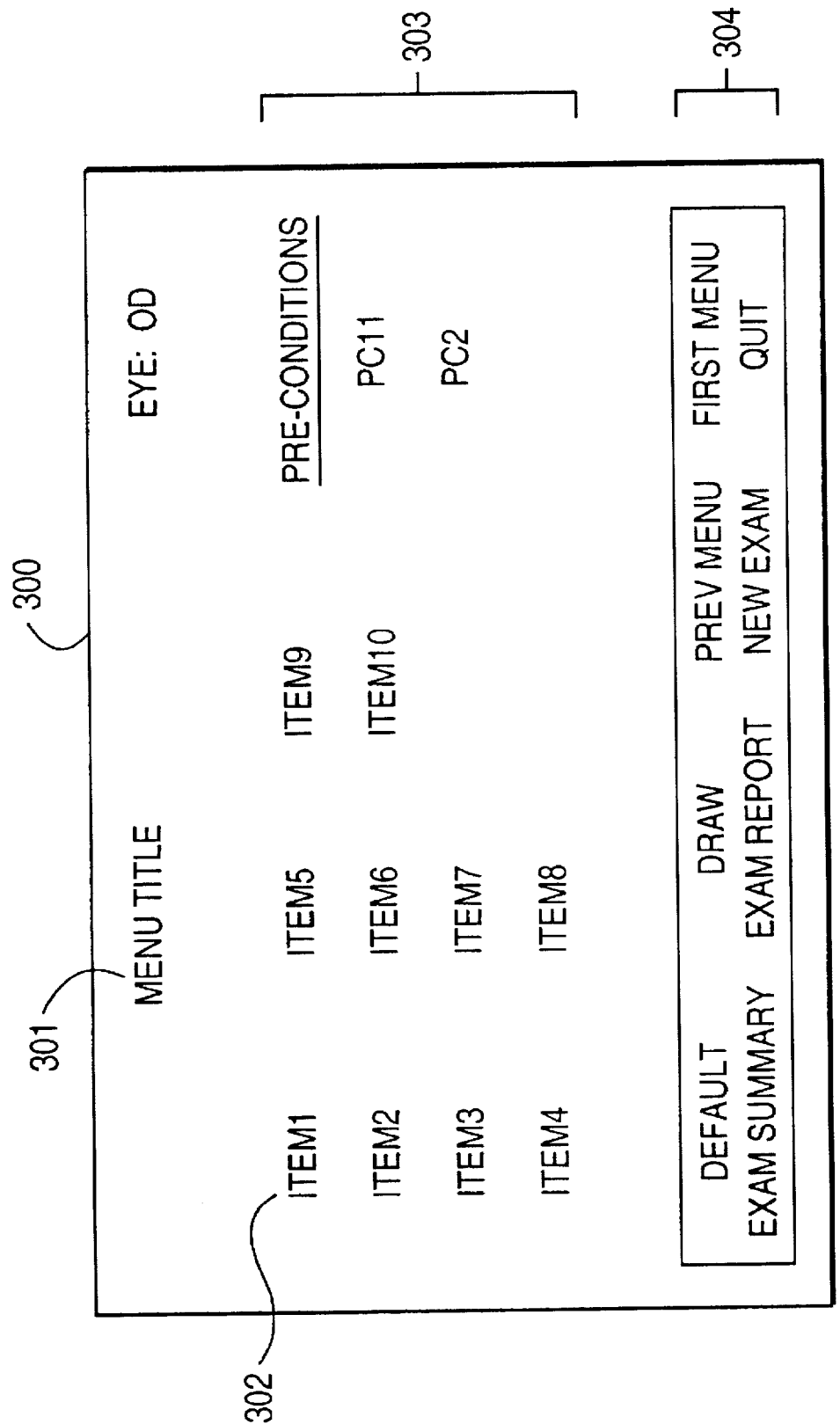
FIG. 3 shows the display format of a menu for exam type and data entries.

The system menus and menu items are programmed as follows. Referring to FIG. 3, the display format of a menu for the exam type and data entries is illustrated. Menu 300 consists of programmable 303 and fixed 304 items. A plurality of programmable items 303 are allowed on menu 300. In a specific embodiment, a maximum of twelve are allowed. Additionally, a plurality of fixed items are allowed on each menu, each with its predefined function. In a specific embodiment, nine fixed items are allowed.

The functions of fixed items 304 cannot be changed by the user. As FIG. 3 illustrates, for example, the following fixed menu items may be defined:

EYE: Provides the selection for OU, OD or OS.
DEFAULT: Attaches the default data values to the selected item.
PREV MENU: Re-displays the previous menu.
FIRST MENU: Displays the first menu for the selection of the type of examination to be performed.
DRAW: Allows the user to draw and/or write on the display screen using the electronic pen.
NEW EXAM: Starts a new exam.
EXAM SUMMARY: Displays selected exam types and data input in a summary format.
EXAM REPORT: Prepares and displays complete exam report based on the user inputs for the current exam.
QUIT: Aborts system operation.

While the user is able to define all twelve programmable items for a menu, it is not necessary that all twelve items be defined.

Again referring to FIG. 3, the following information is required to define a menu:

1. Menu Title 301: The menu identifier displayed at the top of the menu.
2. Current menu number: Each menu is identified by a unique number to be used by the internal data structure of system 100. The menu number is assigned by system 100 at the time of defining the menu.
3. Programmable Menu Items 303: The user is to able to define these items for display on a menu.
4. Fixed Menu Items 304: These are nine fixed items on each menu whose functions are basically the same on all menus.

Figure 4:
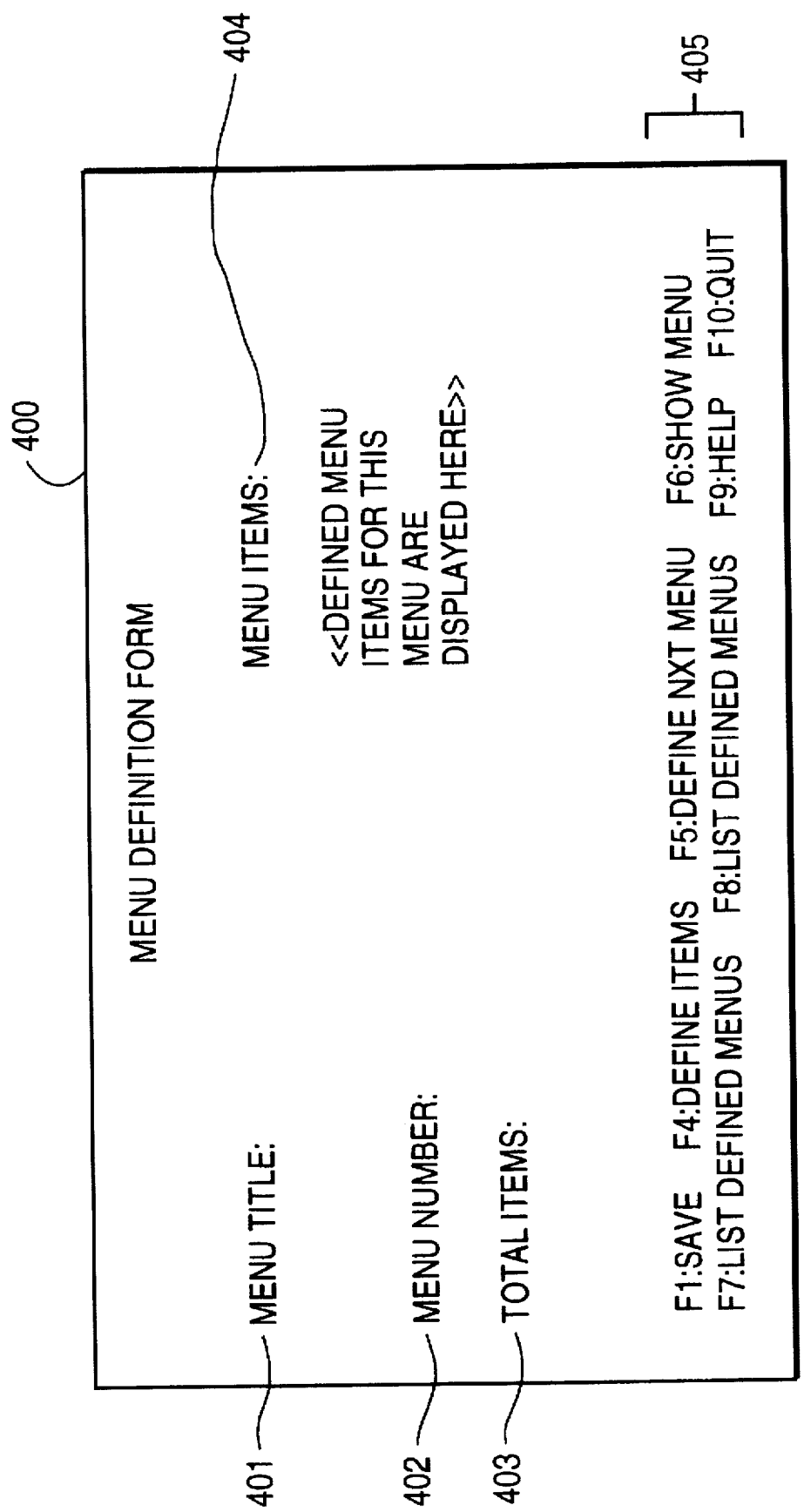
FIG. 4 shows the menu definition form.

Referring to FIG. 4, the operation of programming a new menu is illustrated. After selecting "program system menus and menu items" from the system programming mode menu, menu definition form 400 is displayed. The user enters information for each displayed prompt as follows:

The menu title 401 is used to enter a descriptive title of a plurality of characters, in a preferred embodiment twenty characters or less.

A current menu number 402 is a unique number for the identification of the current menu. In a preferred embodiment, the current menu number is assigned by system 100 with a range from 1 to 1000. In addition, total items 403 ranging from 1 to 12 specify the maximum items for the menu. Menu items 404 is the list of defined items for the menu titled 401.

Function keys 405 of Menu Definition Form 400 are defined as follows:

F1: SAVE: Saves currently displayed menu record in menu definition records' file.
F4: DEFINE MENU ITEMS: Displays the menu item definition form for defining/modifying items' definition for the currently displayed menu record.
F5: DEFINE NXT MENU: Displays blank form for next menu to be defined.
F6: SHOW MENU: Displays the current menu record in exam documentation mode.
F7: LIST UNDEFINED MENUS: Displays the list of all menus to be defined.
F8: LIST DEFINED MENUS: Displays the list of all defined menus. User will be able to select any menu from the displayed list for review/edit purposes.
F9: HELP: Displays on-line help for the user.
F10: QUIT: Aborts menu definition operation and displays the main menu again.

Menu items will now be described in detail. The menu item facilitates the selection of the type of exam and the selection of the type of measurements and observations being taken during the examination.

To define a menu item, the following information is required:

a. Item description: Item description in alphanumeric english text.
b. Item type: A menu item can be one of the following types:
   Title: A menu item which appears as a title on the exam reports.
   Noun: An item describing the type of exam, i.e., Visual acuity, Pupils, Eye movements etc. This item may have text string associated with it.
   Pronoun: An item describing the subcomponents of an exam, i.e., versions, ductions etc. for eye movement exam. This type of item may have text string associated with it.
   Adjective: An item describing the type of observations or measurements to be performed for an exam, i.e., sphere, cylinder and axis for referaction or orthotropia, esotropia etc. for eye movements. These items may have pull down key pads assigned to them. Adjective type item is required to have a string attached to it. If no string is programmed for the item, item name will be used for report generation if item is selected during the exam.
c. Item menu number: Number of the menu where item is displayed.
d. Next menu number: Number of the next menu to be displayed upon selection of this item. The next menu number is valid for the Title, Noun and Pronoun type of items only. During the programming mode, system will keep track for all defined and undefined menus based on the defined title, Noun, pronoun and adjective type items. The next menu number will be assigned by the system. However, this number may be re-assigned to a different menu by the user.
e. Pull down Keypad #: The pull down keypad number is assigned for adjective type items only. If assigned, corresponding keypad will be displayed upon selection of the adjective type time on a menu.
f. Variable string: Variable strings will be programmed for noun, pronoun and adjective type items. The strings will have fixed english text with embedded data variable strings for formatting the user input. Based on the user input during exam documentation mode these strings will be used in the generation of final exam report.
g. Default string: Default strings may be programmed for noun, pronoun and adjective type items. There will be two different kinds of default strings, one applicable for both eyes and the second applicable to only one eye right or left. These strings will have fixed text with the exception of data variable for defining the eye type in the string which is applicable for only one eye. Default strings for an item will be used as follows in the generation of exam report:

i. If data are entered for one eye, second default string will be used for the other eye.
ii. Item is selected but no data are entered. Default string for both eyes will be used.
iii. User chooses to use the default data string for both eyes or for one by selecting <DEFAULT> and then the desired item for one eye or for both eyes.
iv. Default string for both eyes will be used if user selects exam types for inclusion in the report, just prior to the report generation as directed by the system, but there are no exam data present for the selected items.

Figure 5:
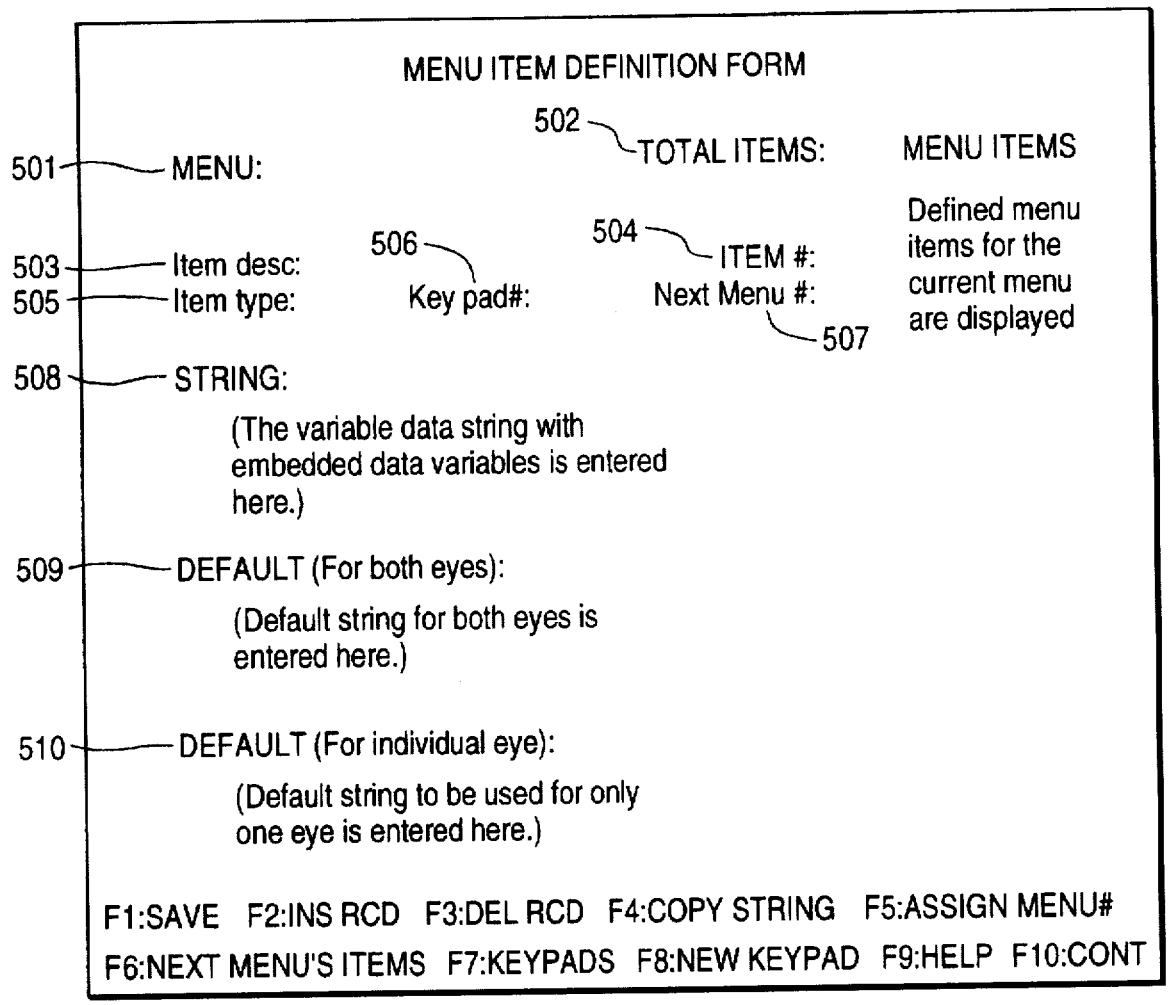
FIG. 5 shows the menu item definition form.

Referring to FIG. 5, the operation of programming menu items is illustrated. The data for defining the menu items are entered on the menu item definition form 500, which is displayed by selecting "define-items" on menu definition form 400. The information for the displayed prompts is as follows. Menu 501, entered by the system, is the menu for which the items are being defined. Total items 502 is the maximum number of items for the menu 501. Item description 503 is a text string, entered by the user, identifying the type of function to be performed upon selection of this item. Item number 504 is sequentially assigned and displayed by system 100 as items are defined for the menu. Item type 505 (selected from title, noun, pronoun, or adjective) is a mandatory field completed by the user.

Pull down keypad number 506 is a number identifying a defined keypad. The user enters the desired keypad in this field. The keypad number is valid only when the item is of type adjective. Next menu number 507 is the menu number for the next menu to be displayed upon selection of this item; it is assigned by system 100. The next menu number is assigned only if the item type is T (Title), N (Noun) or P (Pronoun). String 508 is the narrative or plain text associated with an item. In a preferred embodiment, the text is in English. (In alternative embodiments, string 508 can be written in other languages, e.g., French, German, Spanish, and Russian.) This text is used in formatting the exam report.

Default 509 and 510 represent the default values used in formatting the reports for this item. It may contain, for example, numbers or a text string. This information is included in the exam report when the DEFAULT option is selected for the item. The entered information for the item definition is saved by selecting the SAVE function from function keys 5 10.

After defining the menu item, the data are checked for validity. Next, an internal data structure is created and linked to the proper menu (via its data structure). Subsequent menu items for the same menu are defined in a similar manner after selecting the NEXT function key.

Existing menus may be modified for adding, deleting, or changing the currently defined items of the menu. This requires the search and display of the existing menu definition data on the menu definition form. The displayed information is then edited as desired.

MODIFICATION OF EXISTING MENUS

The existing menus may be modified by adding new items, deleting existing items or by updating the currently defined items for the menu. This will require the search and display of the menu definition record to be modified. The displayed information will be edited as desired.

To display a defined menu's record, a list of defined menus will be requested by pressing F8 key on the menu definition form. The user will then be able to select and display the desired menu's record from the displayed list.

Once the record is displayed, the user will be able to edit the menu title and/or the total number of the items for the menu. If number of items is decreased, no further action will be required except saving the modified record. However, if the number of total items is increased, the extra items must be defined using the 'Define items' option.

MODIFICATION OF EXISTING MENU ITEMS

To update the item definition records for the existing menu items will require the search and display of existing records. This will be accomplished by first displaying the item's menu record as described hereinabove. The item record for the first item of the menu will then be displayed by selecting 'Define items' option on the menu definition form. A desired item record will be displayed by repeatedly pressing PgDn key until the record is located. Displayed item record may then be edited.

B. Pull Down Keypads

There will be several different types of pull down keypads programmed into the system. These keypads will be used for entering numeric data and/or descriptive information for various exams. Pull down keypads will be displayed automatically when adjective type items are selected during the exam documentation if a keypad number is assigned for the selected item. Keypad number is assigned to an adjective type item during the item definition on the item definition form.

Figure 6A:
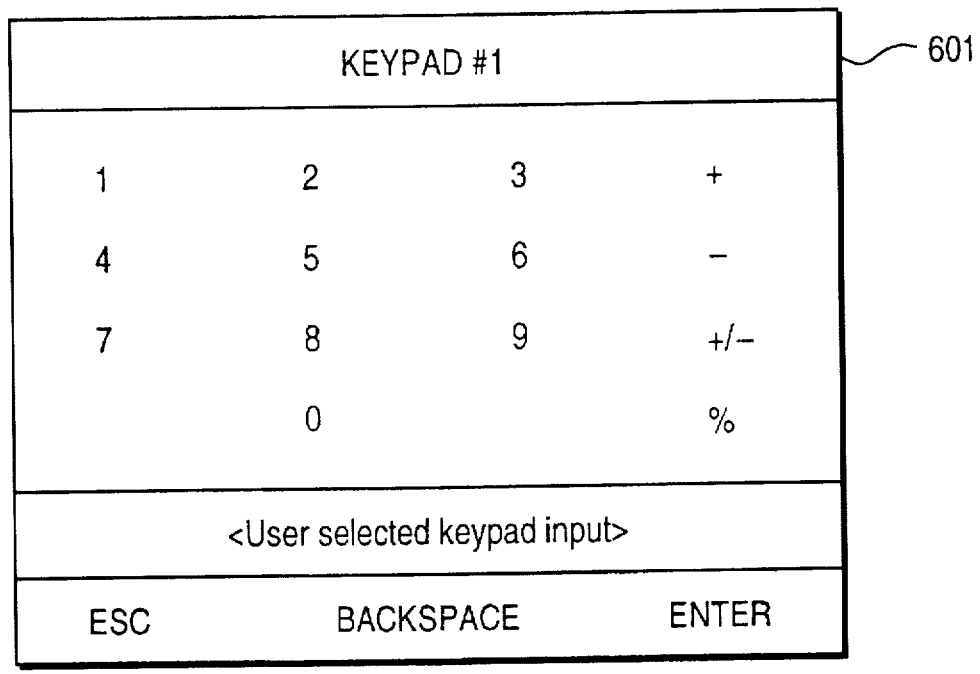
FIGS. 6a, 6b, and 6c show different possible keypads.
Figure 6B:
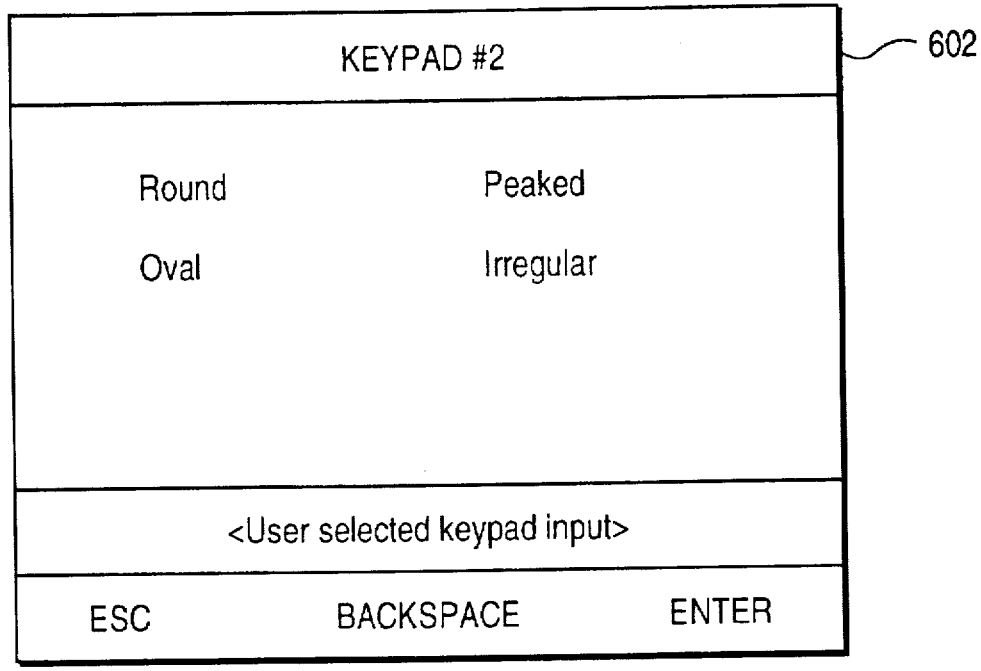
Figure 6C:
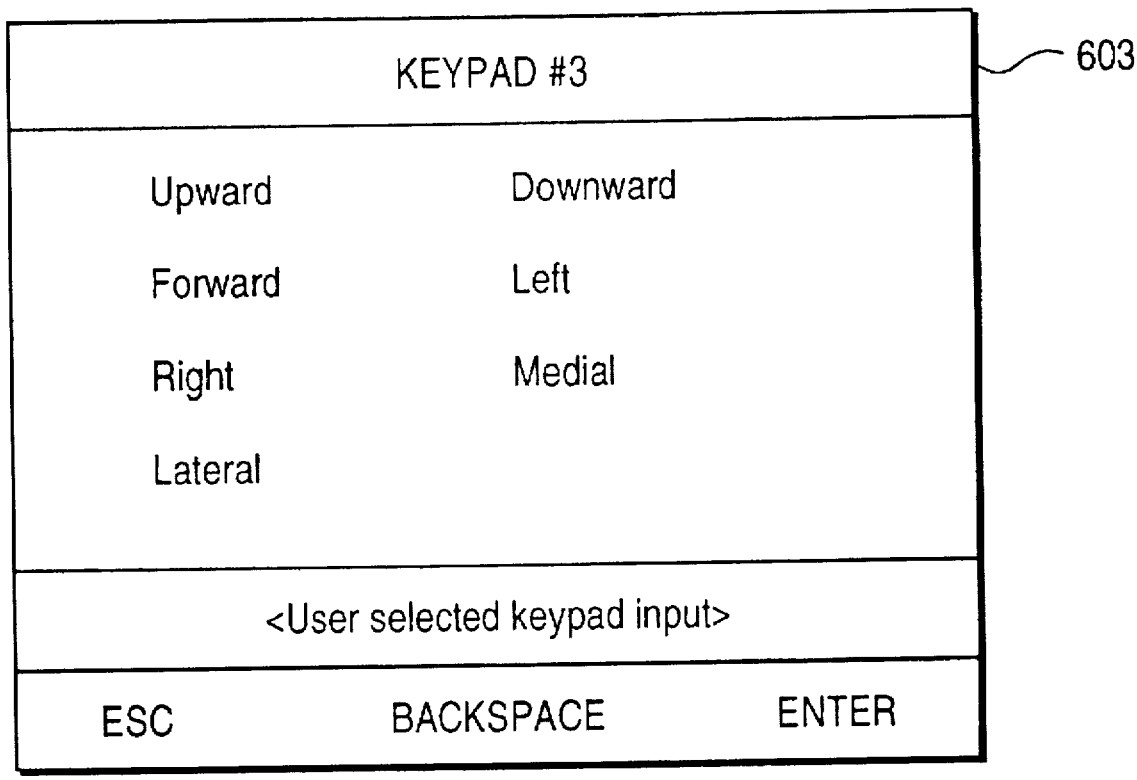

There are different kinds of keypads available based on their association with the different types of exams. However, the use of any keypad is not limited to a particular menu item. Referring to FIGS. 6A–C, different keypads 601, 602, 603 are illustrated.

IV. System Programming Mode: States of Operation

Figure 7:
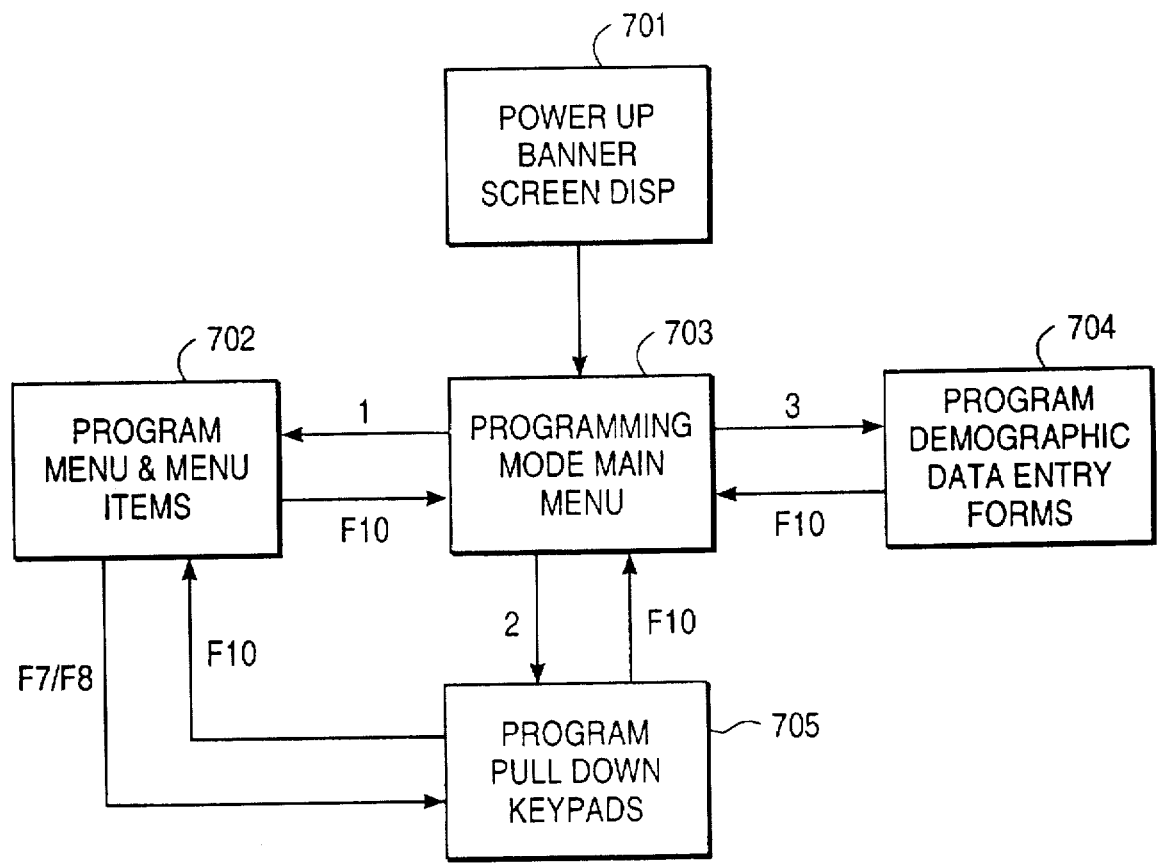
FIG. 7 is a transition-state diagram for the System Programming Mode.

Referring to FIG. 7, the system programming mode has five basic states of operation. Upon start up, system 100 enters Power up banner screen display state 701. In its state 701, hardware diagnostics are performed, and the system parameters are reset.

Upon completion of state 701, system 100 enters Main system menu display state 703. This state displays the system menu from which the user may select the programming modes for the menu and menu items, keypads, or the demographic data entry forms. The next state transition occurs based on the item selected from the system menu.

Upon selection from the system menu (for example, by pressing a "1" key on keyboard 107), system 100 enters Menu and item definition state 702. During this state, the exam selection menus, menu items, text strings, and default data are programmed. The user may exit back to Main system menu 703, for example, by selecting a "F10" key.

Figure 8:
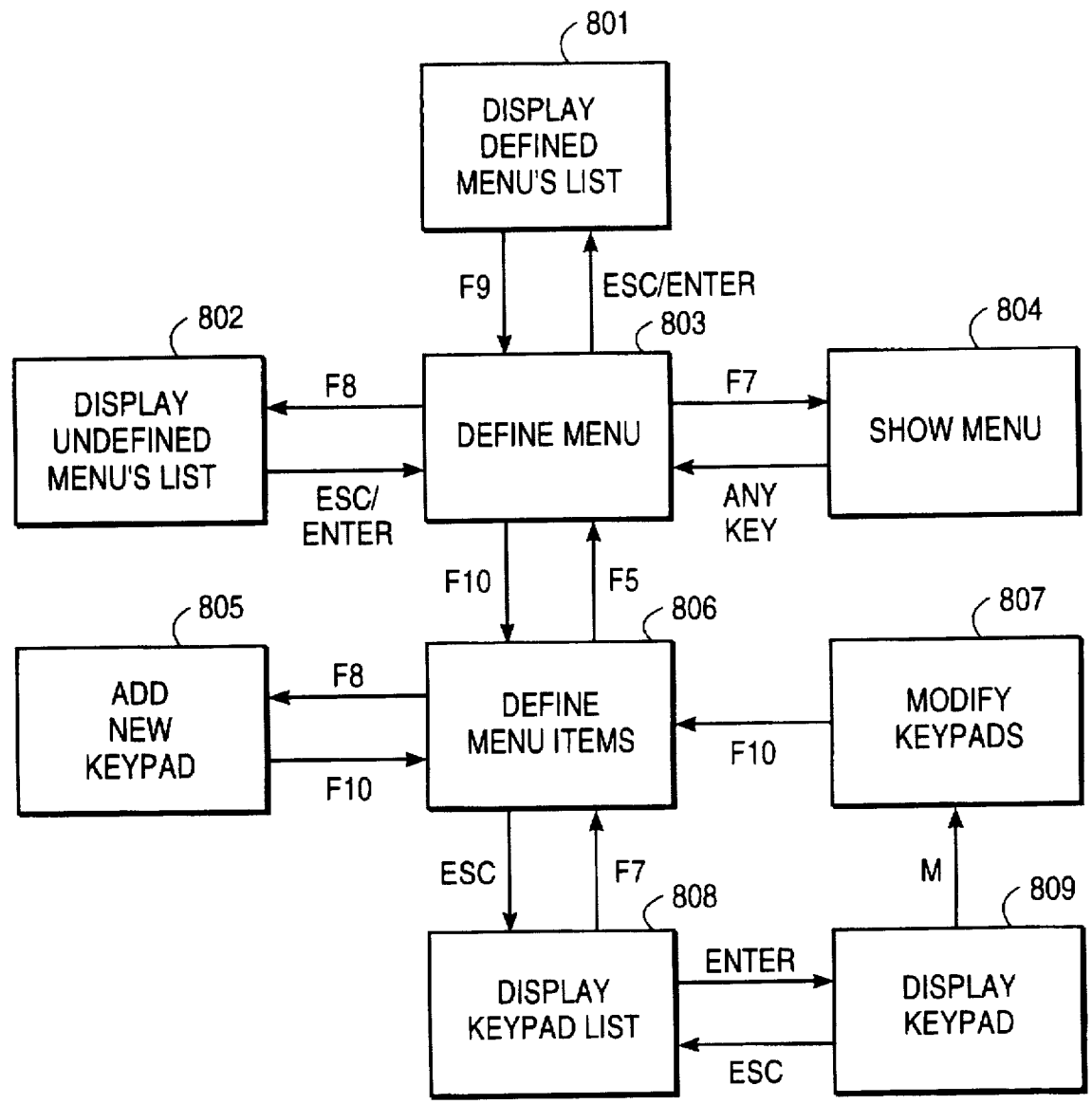
FIG. 8 is a transition-state diagram for the Menu and Item Definition State.

As FIG. 8 illustrates, Menu and item definition state is subdivided into a plurality of substates: Display defined menus' list 801, Display undefined menus' list 802, Define menu 803, Show menu 804, Add new keypad 805, Define menu items 806, Modify keypads 807, Display keypad list 808, and Display keypad 809. Transition between the substates is accomplished by entering an appropriate key from keyboard 107 or screen 104.

Referring back to FIG. 7, in Keypad definition state 705, the pull down keypads are defined. State 705 is entered either from Main system menu 703 (e.g., by selecting "2") or from Menu and item definition state 702 (e.g., by selecting "F8"). In the latter case, state 705 also allows the modification of existing keypads and the addition of a new keypad.

Programming of demographic data entry forms state 704 is entered from Main system menu 703 (e.g., by selecting "3"). In state 704, demographic data entry forms are developed and customized. States 704, 702, 705 are terminated by returning to Main system menu 703 (e.g., by selecting "F10").

V. Eye Exam Documentation Mode

In this mode of operation, the user documents the eye exam using pre-programmed system menus, menu items, and keypads. Supplemental data, for example, patient demographic information, is also entered in this mode. In addition to documentation of the eye exam, the user can generate a hard copy printout of the exam report, transfer patient demographic and exam data to a host computer for editing and archiving, and retrieve existing data from the host system into system 100.

Figure 9:
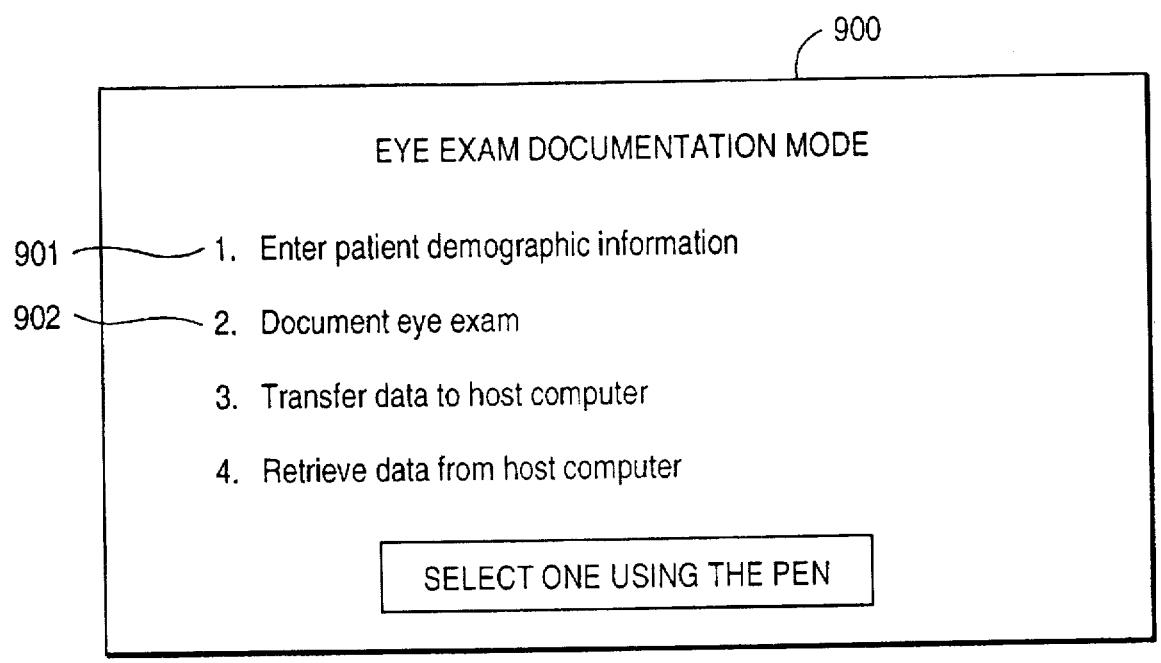
FIG. 9 shows the eye exam documentation mode menu.

Referring to FIG. 9, upon entering the Eye Exam Documentation Mode 202, the corresponding menu 900 is displayed. From this menu, the user selects one of the available functions.

Upon selecting "enter patient demographic information" 901, the user may enter the demographic information, past medical history, and other relevant information for a patient by using programmed demographic data entry forms. In a preferred embodiment, this information is entered with detachable keyboard 107. While this information is not necessary before the eye exam data are entered, minimum demographic information can be required before a report is generated. The criteria for the minimum required information is defined during the programming of the demographic data entry form.

When "document eye exam" function 902 is selected on menu 900, the first programmed menu for the selection of type of exam is displayed. The eye exam itself is documented by touching the displayed menu items on the subsequent menus and pull down keypads associated with the type of exam selected. Since there is no data entry using the keyboard while performing and documenting the eye exam, the keyboard 107 may be detached from system 100 at this stage. Additional information is entered by writing on screen 104; it is stored for later reporting (in the same graphic format as entered).

Thus, a typical procedure for documenting the eye exam is as follows. First, the patient's demographic information and medical history data are entered by ancillary personnel using keyboard 107 and data entry forms. Next, the keyboard 107 is detached from system 100. At this point, system 100, which is essentially a pre-programmed electronic writing pad capable of storage (by main memory 102 and/or mass storage 106), is provided to the physician.

The physician selects the type of exam to be documented by touching the display menu item on system screen 104. The physician then documents the exam by touching the corresponding exam descriptor and corresponding data items on the subsequent menus. When appropriate, the pull down keypads are used to document the exam results. Additional information is entered by writing on the screen 104 with pen 105.

After completion of the exam, system 100 interprets the physician's input and prepares a complete written report or document containing the exam data as well as the patient's demographic information. This document can be stored on storage device 106, printed on printer 108, or communicated to host computer system 150 via communication port 109. This approach provides remote storage for a large number of patient data which may be retrieved at a later date as needed. In addition, this alleviates the need for system 100 to have additional word processing capabilities. For follow-up exams, pertinent demographic medical history information and previous exam data may be retrieved from host 150 via port 109.

Figure 10A:
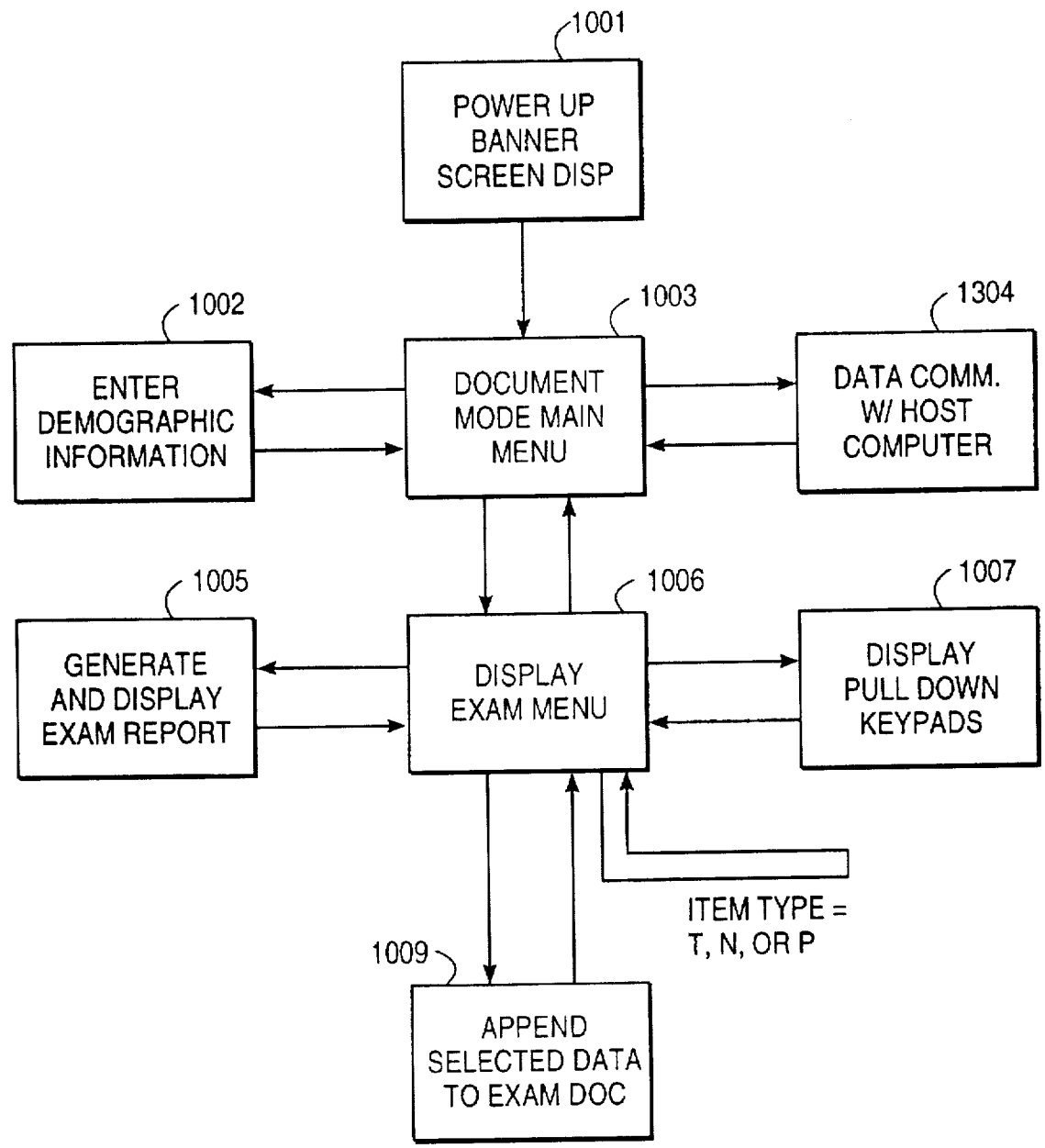
FIG. 10 is a transition-state diagram for the exam documentation mode.
Figure 10B:
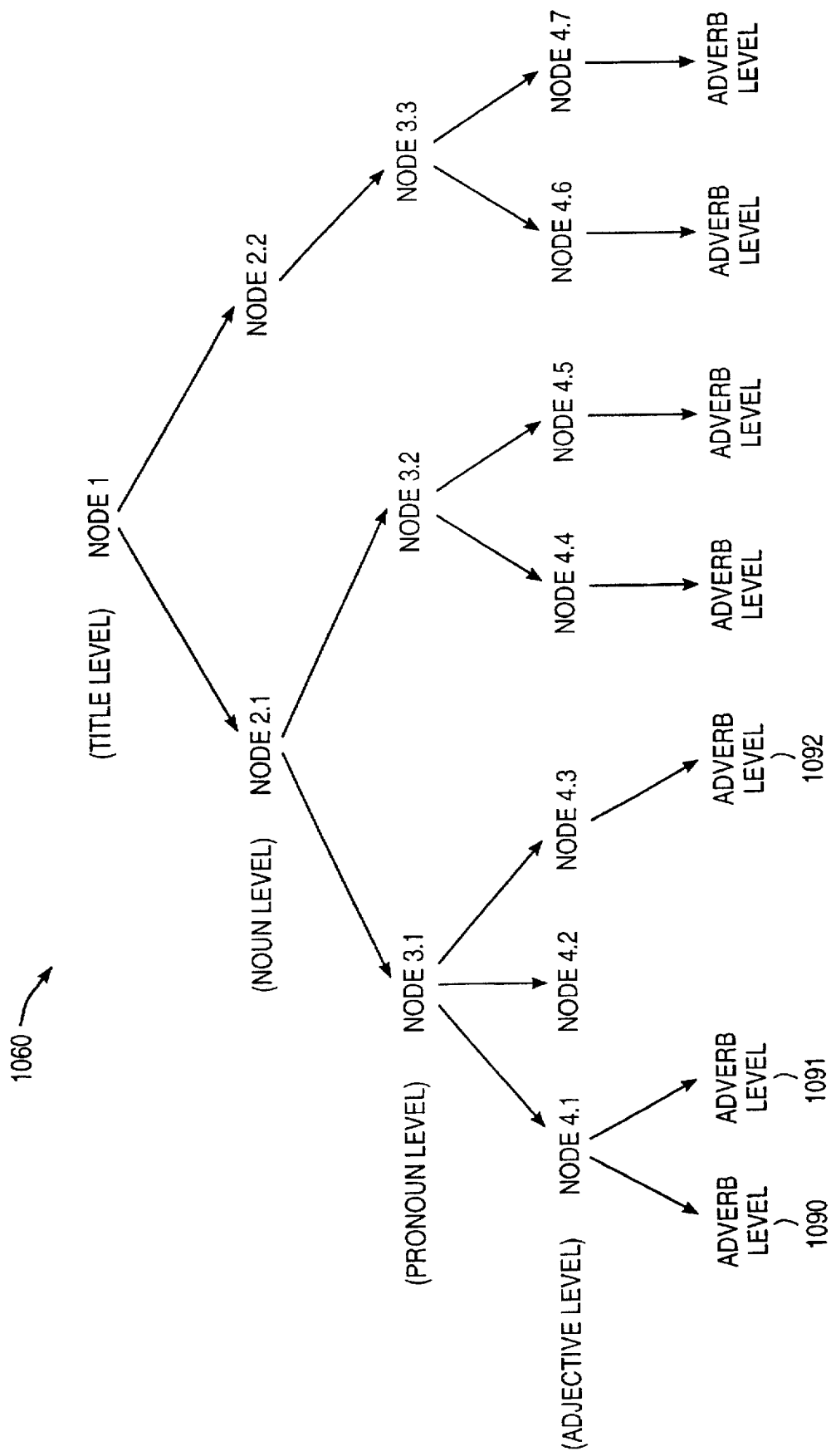
Figure 10C:
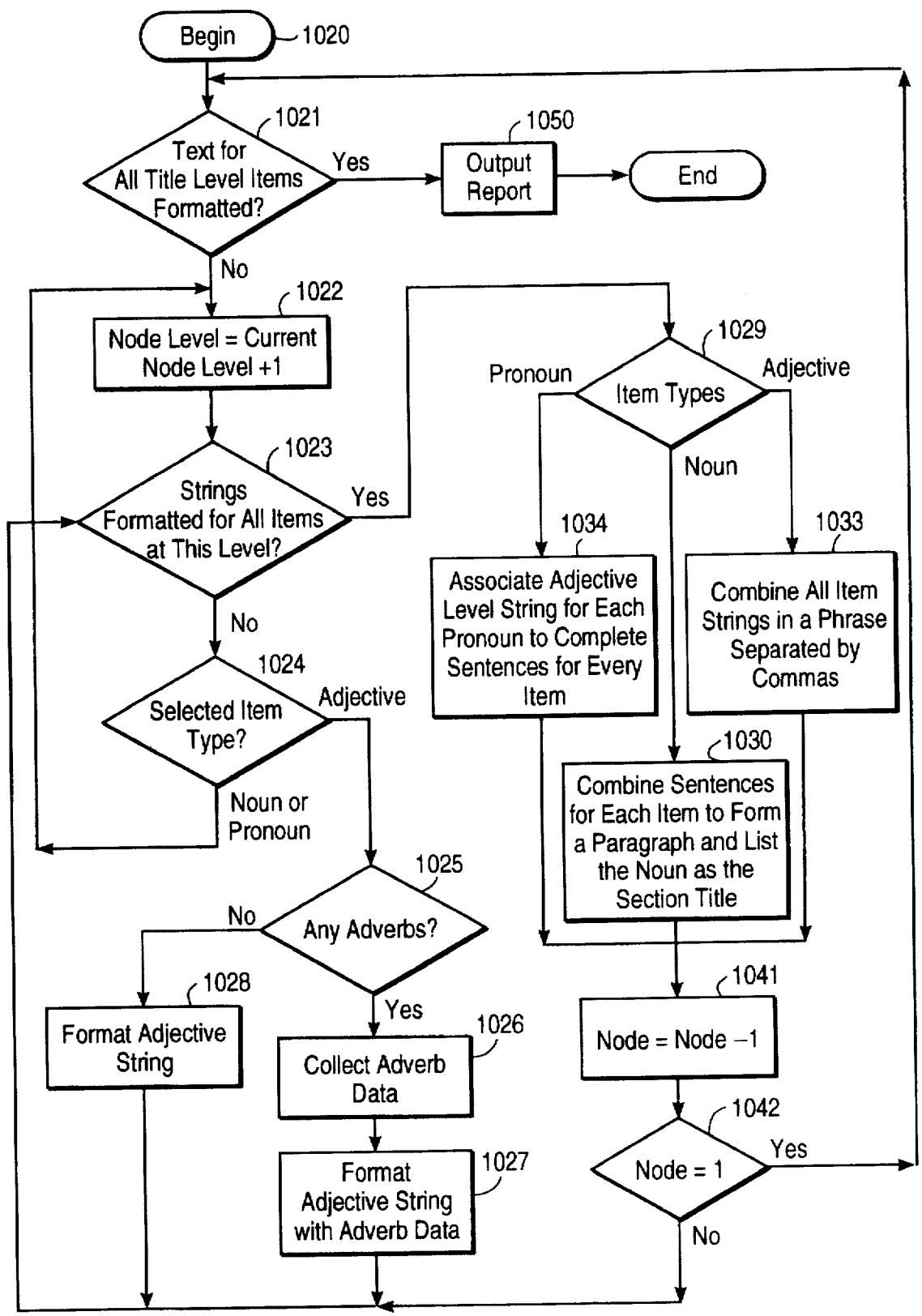

Referring to FIG. 10, the transition states for the Exam Documentation Mode are illustrated. Power up system diagnostics state 1001 performs the same functions as diagnostics state 701. Upon exiting state 1001, system 100 enters document mode main menu from which one may enter the Exam menu display state 1006. This state displays the exam selection menus. During the exam mode, system 100 spends most of its time at this state.

State 1006 is reentered to display the next menu every time a "T", "N", or "P" type item is selected on the currently displayed menu. When an "A" type item which has no pull down keypad assigned is selected, the system enters Data append state 1009 and appends the selected menu item to the exam document. After appending, system 100 automatically returns to Exam menu display state 1006. State 1009 may also be entered from keypad state 1007. In either method of entering the state, the selected data are saved and appended to an exam documentation data buffer. During generation of the report, the entered data items are formatted into the plain English text using the pre-programmed text strings.

Pull down keypad display state 1007 is entered when an "A" type item having an assigned keypad number is selected. The keypad assigned to the item is displayed. The user selects keypad items followed by the <enter> key. In response, the keypad items are appended to the selected item. Selecting an ESC (escape) key aborts keypad data entry.

Demographic data entry state 1002 is entered from main menus state 1003. In state 1002, the patient's demographic data are entered. These data are then included in the exam documentation reports.

Generate exam documentation report state 1005 is entered from Display exam menus state 1006. In state 1005, a complete exam report is generated based on the selected menu items, data from the pull down keypads, preprogrammed text strings and default data strings. The generated report is saved on storage 106 for future retrieval and/or printed by printer 108.

VI. System Software Requirements

System 100 can be divided into two major categories of operation: (1) operation under system programming mode, (2) operation under exam documentation mode, separate software for each category.

VII. Function Control Software

A. System Programming Mode Software

Figure 11A:
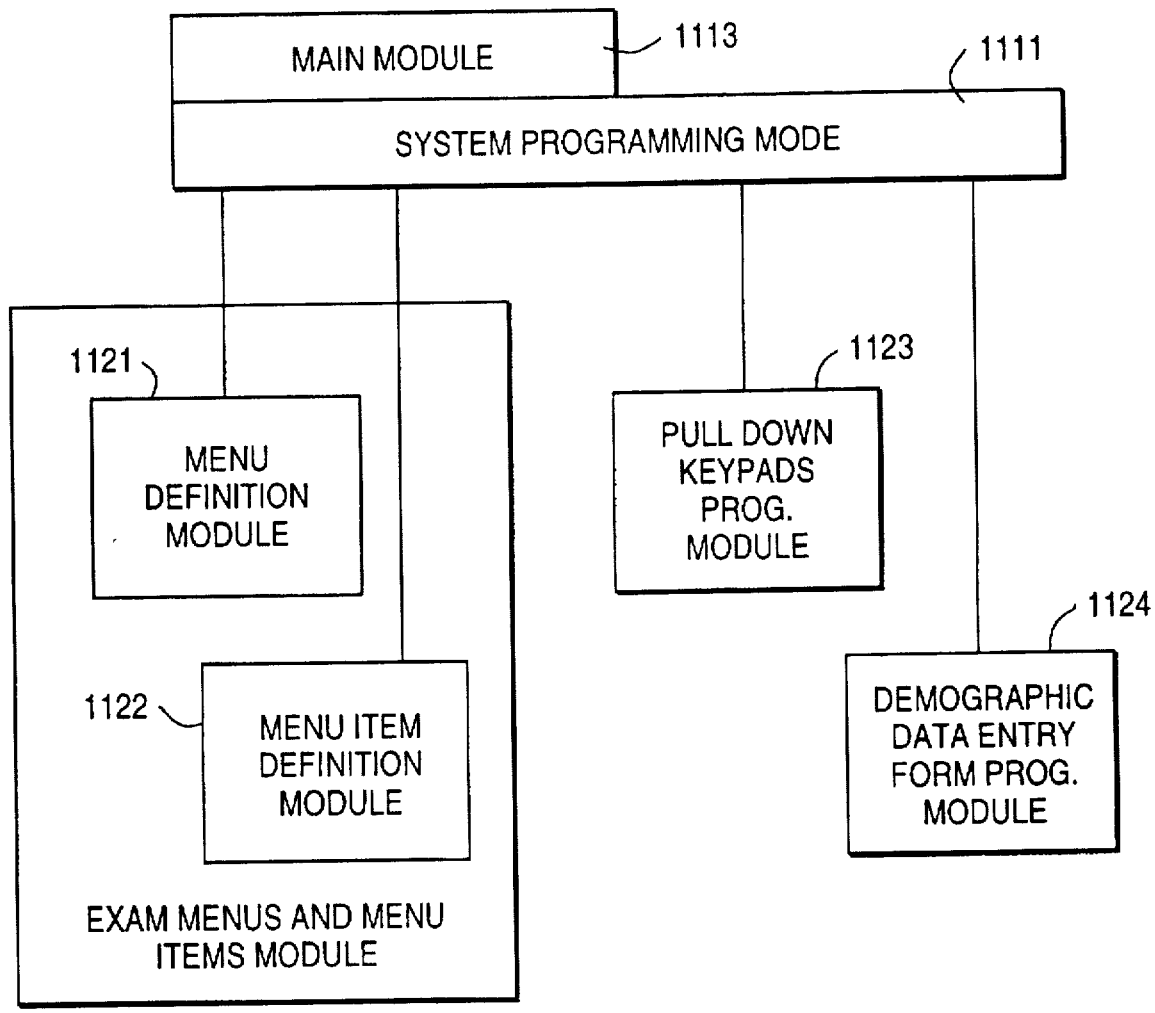
FIG. 11A is a block diagram showing the relationship of the function control software with other software modules for the system programming mode.
Figure 11B:
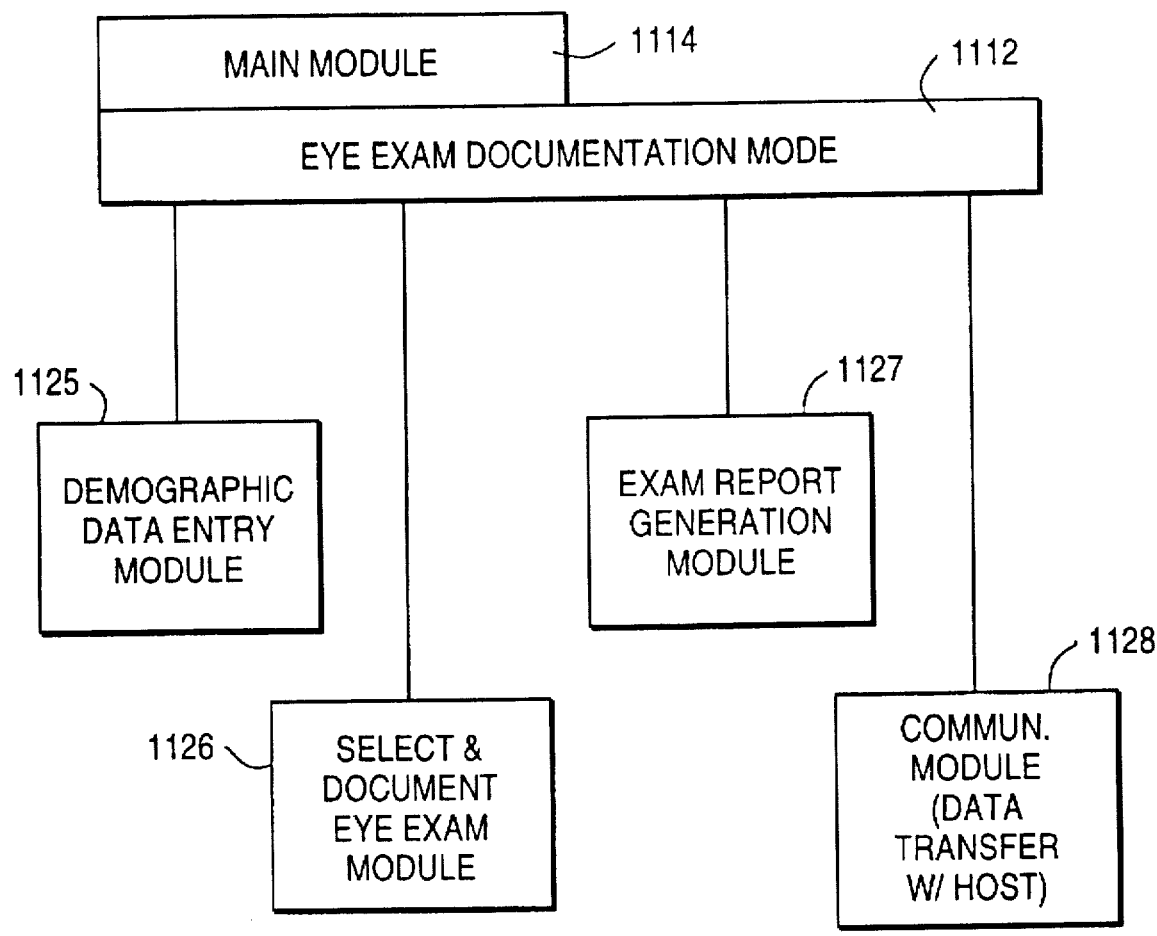
FIG. 11B is a block diagram showing the relationship of the function control software with other software modules for the exam documentation mode.

Referring to FIG. 11A, the System Programming Mode Software 1111, permits the user to program and customize system 100 for eye exam documentation menus, menu items, keypads, and demographic data entry forms. Mode 1111 may be divided into three main functions or modules: (1) programming of exam menus and menu items 1120, (2) programming of pull down keypads 1123, and (3) programming of demographic data entry forms 1124. Module 1120 may be subdivided into a menu definition control module 1121 and a menu item definition control module 1122.

Each function of system 100 is represented by a separate control module. A main module 1113 for the program mode operation directs the transfer of software control to the corresponding programming function control module 1101 based on user input. There is no direct transfer of control among the three major programming function modules.

1. Software for Programming the Exam Menus and Menu Items

Module 1120 is responsible for displaying the menu and menu item definition data entry form, accepting the user input, and interpreting the input data. This software also creates the internal data structure linking all menus, menu items, and text strings used in formatting the exam reports. The data structures created are based on user input for the menu and menu item definitions.

The main functions of module 1120 are: (1) display menu definition form, (2) display menu item definition form, (3) accept user input and check its validity, (4) locate and display previously defined information for menu and menu item definition, (5) interpret the user input and create internal data and link structure for menu and menu items, and (6) save created data structure for use during the exam documentation mode.

2. Software for Programming the Pull Down Keypads

Pull down keypads programming control module 1123 controls the pull down keypads, which are for general use throughout the system operation. Upon selection of a menu item, the keypads are automatically displayed on top of the current display menu (if so desired in the menu item definition). The main functions of module 1123 are:

a. Display keypad definition form.
b. Accept user input for keypad title, keypad type and for keypad items. Check input data validity.
c. Locate and display previously defined keypads.
d. Save keypad definition record.

3. Software for Programming the Demographic Data Entry Forms

Demographic data entry form programming control module 1124 allows the user to display the currently programmed data entry forms. The user is able to customize these forms as desired within a set criteria. Module 1124 is divided into various submodules for displaying and redefining forms. Module 1124 directs communication among the submodules.

The main function of module 1124 is to a. Display currently programmed demographic data entry forms.
b. Accept user inputs for adding additional data entry fields, and for deleting or modifying the existing data entry fields.
c. Check the validity of the user input for form and data entry field definitions.
d. Save newly created forms for their subsequent use during exam document mode.

B. Eye Exam Documentation Mode Software

Eye exam documentation mode software 1112 facilitates entering patient demographic information and eye exam data which are used in preparing the eye exam reports. The mode 1112 is divided into the following major functions: (1) demographic data entry, (2) selecting and documentation of the eye exam, and (3) data transfer between system 100 and a host computer.

Each function of the exam documentation mode is controlled by a separate module. A main module 1114 for the Eye Examination Documentation Mode directs the transfer of separate controls to the corresponding function control module based on user input.

1. Software for Demographic Data Entry

Demographic data entry module 1125 is responsible for displaying the demographic data entry forms and for accepting the data entry for patient demographic and medical history. Module 1125 facilitates the search and display of previously stored patient data.

In a preferred embodiment, the patient data are archived on a host system, thus, the search request from system 100 is processed only when system 100 is connected with host computer 150, for example, through communication port 109. Module 1125 sends the specified search criteria to host system 150. If the desired patient record is located, the data are transmitted back to system 100 through port 109. This data are then subsequently displayed in the demographic data form.

Module 1125 functions to display data entry forms; accept data entry for patient demographic and medical history; store entered data on system 100 storage media; accept requests for data retrieval from host computer 150; send requests to host computer 150 for data retrieval; accept data from host computer 150 for display at system 100; and transfer data to host system 150 for archiving purposes.

2. Software for the Selection and Documentation of Eye Exams

Document eye exam module 1126 displays the menus and accepts user input for the selection of exam types and entry of exam results. It also accepts additional user input from the electronic writing pad to be included in exam reports. This software functions to display exam menus for the selection of the exam types; display subsequent menus for the selection of exam descriptors; display pull down keypads as required for the input of exam results; accept information entered by writing on the electronic writing pads; interpret the user information and format exam reports using the entered exam data and the text strings programmed in the system (corresponding to the type of exam being performed); and save the exam data and reports on mass storage 106.

3. Software for Exam Report Generation and Printout

To save storage space on the system storage device, the patient demographic and exam data are not stored in final report format. Instead, the file report is generated only when requested to be displayed or printed out by the user. Exam report module 1127 generates the exam report based on the entered demographic data, medical history data, and the eye exam data for the patient.

4. Software for Data Transfer Between Ocuchart and the Host Computer

Communication module 1128 contains the necessary communication functions to transfer patient data between system 100 and host computer system 150.

C. Internal Data Structures

During the system programming mode, the exam menus, menu items, and data items are defined. Internally, these are stored in a format defined by the system data structure. The internal data structure establishes the relationship among the system menus and menu items. This is utilized by the system software in generating the system function menus and data input menus.

The output reports are generated based on the text strings defined in the data structures. In addition, text strings are formatted and manipulated based on the embedded data variables within and outside the text strings.

In operation, System 100 uses the following data files: SPMR.DAT, MENU.DAT, ITEM.DAT, KPD.DAT, STR.DAT, and DEF.DAT. Each file will now be described in detail.

1. SPMR.DAT: System Parameters File

The system parameters which are utilized during the system programming mode are stored in the system parameters file. These parameters provide the next available record indexes for saving the information in the corresponding files during menu, menu item, and keypad generation.

Figure 12:
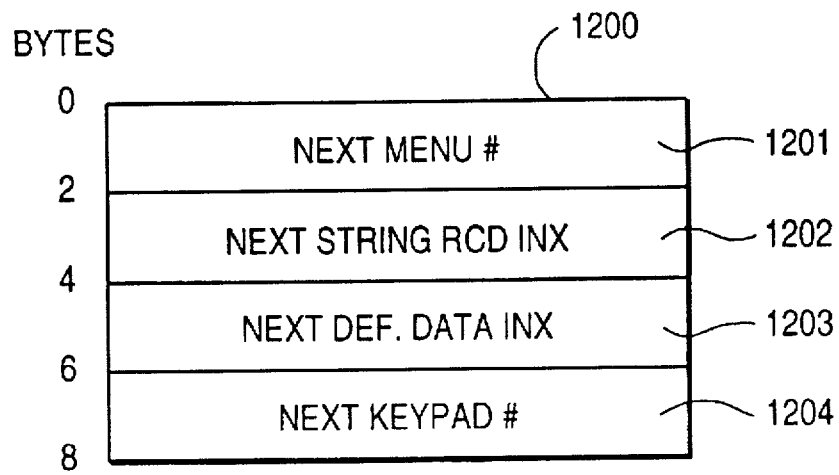
FIG. 12 illustrates the system parameters file.

Referring to FIG. 12, the file structure is illustrated. In a preferred embodiment, SPMR.DAT stores data in a record 1200 which comprises four fields 1201, 1202, 1203, 1204, each field occupying two bytes. Next menu number 1201 is incremented every time the number is assigned to a menu. Next string record index 1202 serves as an index to the text strings' file. This index provides the record number for saving the next string attached to a menu item. After the current index is used for saving the text string, the index is incremented.

The next default data record index 1203 is an index into the default record file. This index provides the record number for saving the next default data/text string attached to a menu item. The index is incremented after the current index is used for saving the default data string (in DEF.DAT file). Next keypad number 1204 is the number assigned to the next program pull down keypad. The number is initialized to 1 when the system parameters file is created, and it is incremented every time the current number is assigned to a keypad.

2. MENU.DAT: Menu Data File

Figure 13:
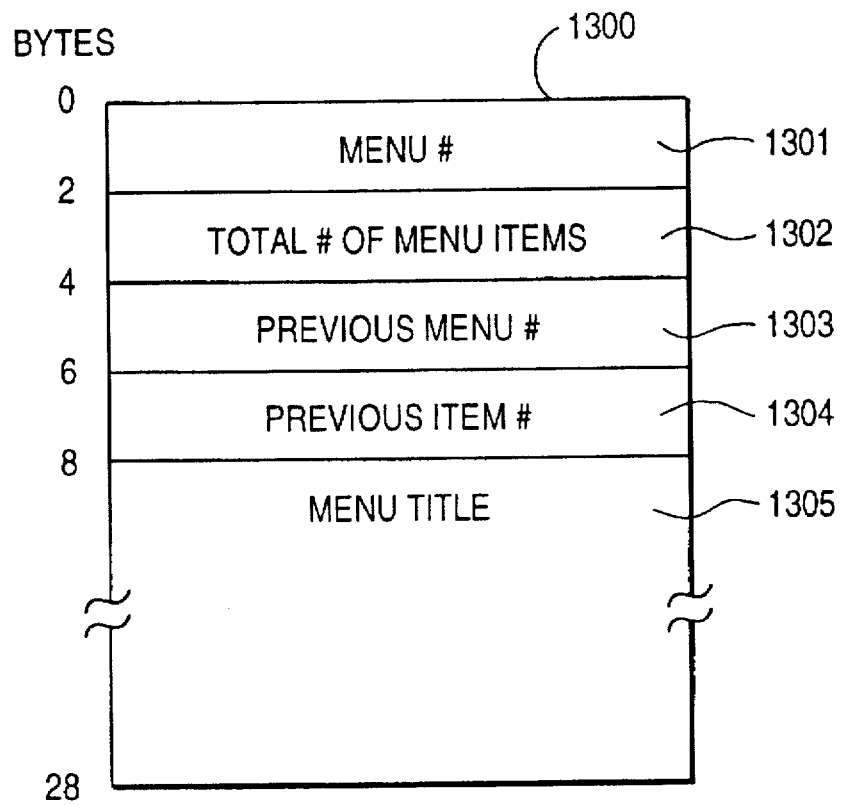
FIG. 13 illustrates the menu data file.

Menus' definition data of system 100 are stored in the menu data file. Referring to FIG. 13, one file record 1300 is used for saving the data for each menu. In a preferred embodiment, the maximum number of menu records in the menu data file are 1000.

Each of the 1000 records in MENU.DAT contains three fields. Menu number 1301 is the menu number assigned to the menu. This is assigned by the system 100 and cannot be altered by the user. Total number of menu items 1302 contains the number of menu items entered by the user for the menu.

Previous menu number 1303 is the number of the menu which is displayed before the display of current menu. Previous item number 1304 is the number of the item on the previous menu which is selected to display the current menu. The previous menu number and the previous item numbers are assigned by the system 100 and cannot be altered by the user. For the very first menu of the system 100 the menu number 1303 and item number 1304 are set to 0. Menu title 1305 is a text string for the menu title. This title is displayed at the top of the menu during the exam documentation mode.

3. ITEM.DAT: Menu Item Definition File

The definitions for the menu items are stored in ITEM.DAT. Since a maximum of twelve items are allowed on a single menu in a preferred embodiment, twelve consecutive records are allocated in the item definition file; each record stores the item definitions for a menu. The allocated records are left unused when a menu consists of less than twelve items. In a preferred embodiment, a total of 12,000 records are allowed.

Figure 14:
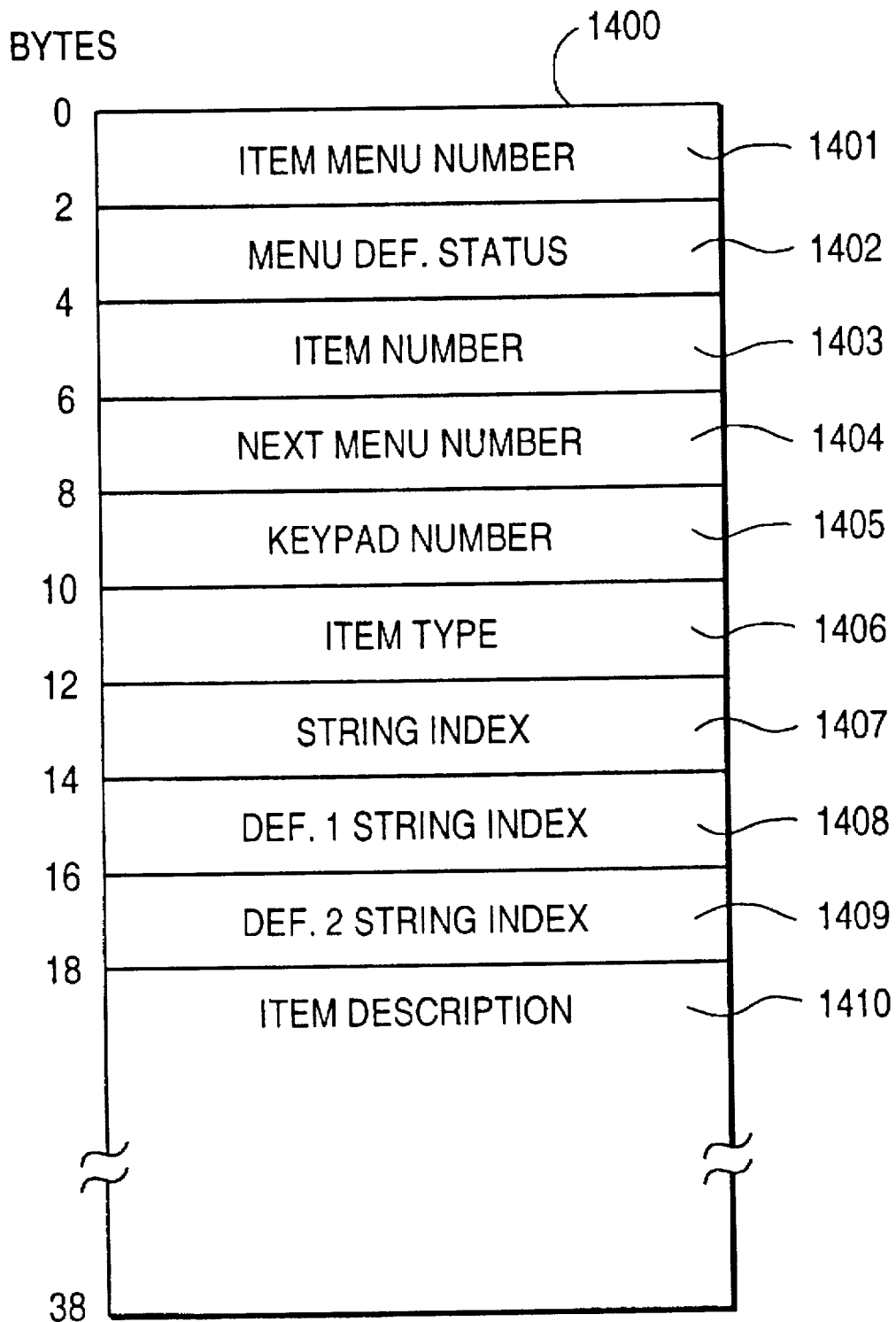
FIG. 14 illustrates the menu item definition file.

Referring to FIG. 14, the file structure is illustrated. In record 1400, the first field is item menu number 1401, which is the menu number for an item. Menu definition status word 1402, contains the status word which is set and updated by system 100 based on user action. No next menu is to be defined for an item, if the item is of type "A". If the item is of type "T", "N", or "P", a menu needs to be defined for an item.

Data item 1403 is a number ranging from 1 to 12 which is assigned to the item by the system sequentially as the items are defined by the user. Next menu number 1404 is assigned by the system and saved at this location if the entered item is of the type "T", "N", or "P". The assigned menu is displayed upon the selection of this item during the exam documentation mode. Keypad number 1405 is entered by the user for an A-type item. Item type 1406 stores one of the following types:

1. T = Title
2. N = Noun
3. P = Pronoun
4. A = Adjective
5. C1 ... C3 = Pre-condition group 1 to 3

String index 1407 is a record index into the string data file for saving the string text for the item. When no text string is entered, the index is set to 0. Default string index 1408 and 1409 are the indexes into the default data file for saving the default text strings for the item. The indexes are set to 0 if there are no default data. Item description 1410 is a text string displayed on the corresponding menu which describes an item. It is also displayed as the title for the next menu if the item is of type "T".

4. KPD.DAT: Pull Down Keypad Definition File

The pull down keypads are used to select and enter numeric data and descriptive words associated with a menu item during the eye exam documentation mode. The keypads are displayed only for the "A" (adjective) type items.

Figure 15:
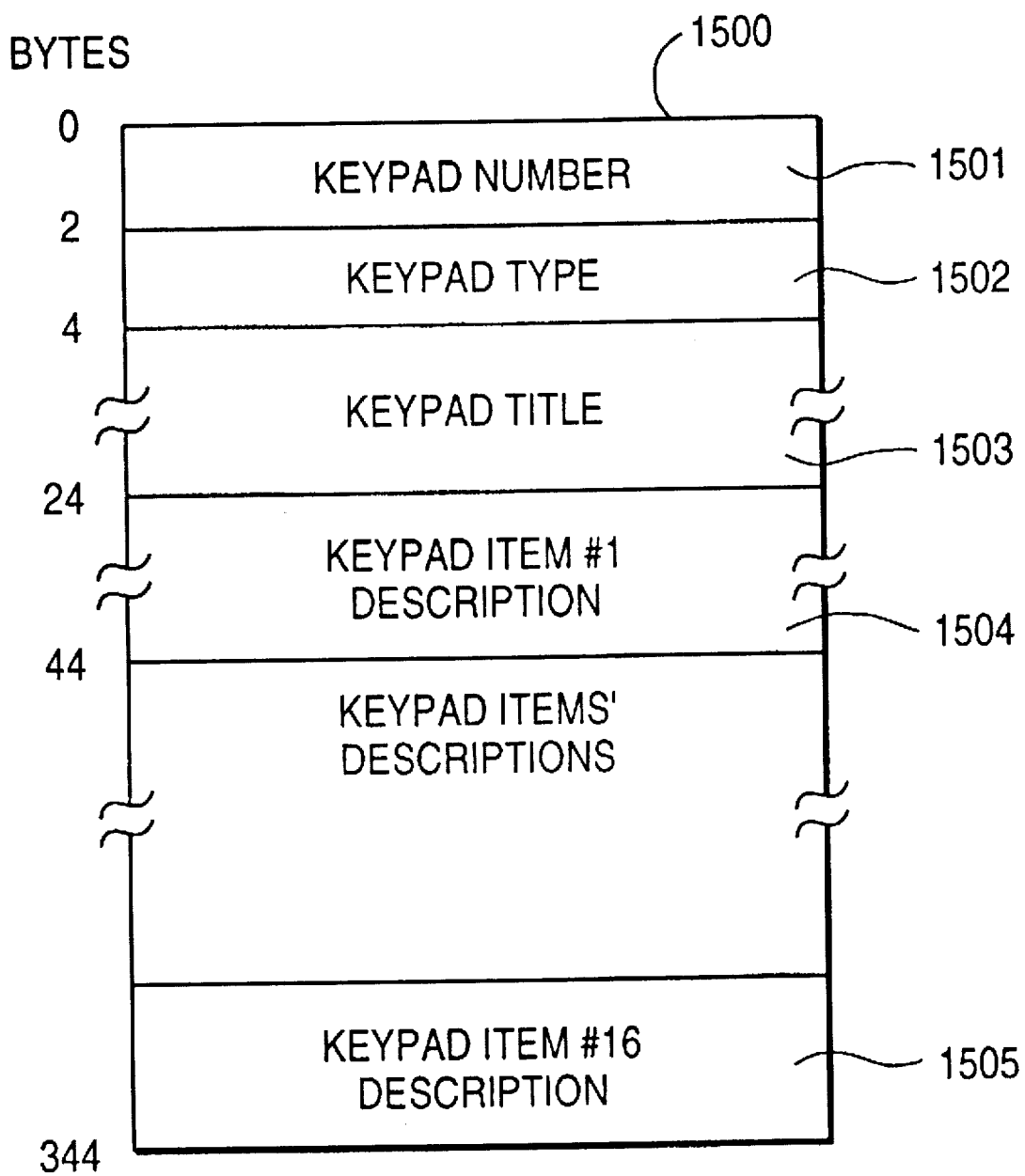
FIG. 15 illustrates the pull down keypad definition file.

Referring to FIG. 15, the file structure is illustrated. KPD.DAT stores data in a plurality of records. (In a preferred embodiment, the maximum number of records is 200.) Each record comprises five fields. Keypad No. 1501 is a number ranging from 1 to 200, with System 100 assigning this number. Keypad type 1502 identifies whether the keypad items are the numeric digits or the descriptive words. The descriptive words are separated by commas when selected during exam documentation mode. The numeric digits, on the other hand, are appended together when the keypad items are selected during the eye exam documentation mode. Keypad title 1503 is a text string for the keypad. Bytes 24 through 344 store the keypad item descriptions (for example, 1504, 1505). Each keypad item description field stores the keypad item descriptions. In a preferred embodiment, each field is 20 characters long, and a maximum of sixteen items can be entered for display on a keypad.

5. STR.DAT: Text String File

Figure 16:
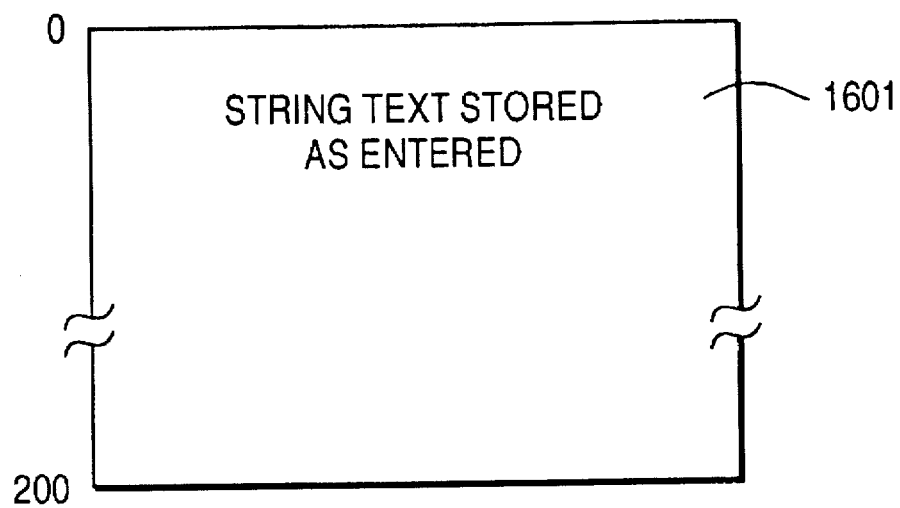
FIG. 16 illustrates the text string file.
Figure 17:
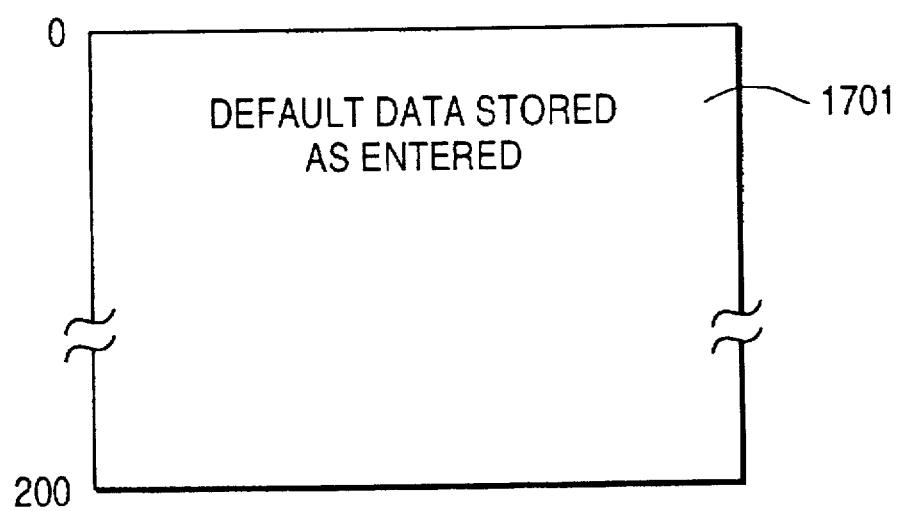
FIG. 17 illustrates the default data file.

Referring to FIG. 16, the text string file stores the text strings attached to the menu items. In a preferred embodiment, a fixed length record 1601 of 200 bytes is allocated for each text string and a total of 1,000 records are permitted. The allocated record number is saved in the corresponding item record in the item definition file.

6. DEF.DAT: Default Data File

The default data file stores the default data strings attached to the menu items. A fixed length record 1701 of 200 bytes is allocated for each default data string. The allocated record number is saved in the corresponding item record located in the item definition file. The entire record of 200 bytes is used to store the entered default data string attached to the menu item.

The above description is illustrative and not restrictive. Many variations of the invention will become apparent to those of skill in the art upon review of this disclosure. Merely by way of example while the invention is illustrated primarily with regard to a physician's system for generating reports, the invention may be applied to a wide variety of addtional report generation systems. The scope of the invention should, therefore, be determined not with reference to the above description, but instead should be determined with reference to the appended claims along with their full scope of equivalents.

What is claimed is:

1. In a programmed portable computer system, said system having a first mode for set up and customization and a second mode for collecting information, a method for generating written reports based on succinct input from a user comprising the steps of:

a) selecting said first mode for set up and customization;
   b) in said first mode, defining a plurality of menus for entering information comprising:
      selecting a menu title for identifying a menu;
      assigning a current menu number for uniquely identifying said menu by said system; and
      providing a plurality of menu items for said menu including providing a plurality of programmable menu items which are changeable by the user and providing a plurality of fixed menu items which are not changeable by the user;

c) selecting said second mode for collecting information;

d) in said second mode, entering information using said defined plurality of menus;

e) interpreting said entered information to format a written report based on said entered information; and f) generating said written report in response to said interpreting step;

wherein said providing a plurality of fixed menu items step comprises:
providing an "Eye" item for selecting one of right, left, and both eyes;
providing a "Draw" item for drawing and writing;
providing a "Default" item for attaching a plurality of pre-established default values;
providing a "Prev Menu" item for redisplaying a previous menu; and
providing a "First Menu" item for displaying a first menu.

2. In a programmed portable computer system, said system having a first mode for set up and customization and a second mode for collecting information, a method for generating written reports based on succinct input from a user comprising the steps of:

a) selecting said first mode for set up and customization;

b) in said first mode, defining a plurality of menus for entering information comprising:
selecting a menu title for identifying a menu;
assigning a current menu number for uniquely identifying said menu by said system; and
providing a plurality of menu items for said menu;

c) selecting said second mode for collecting information;

d) in said second mode, entering information using said defined plurality of menus;

e) interpreting said entered information to format a written report based on said entered information; and f) generating said written report in response to said interpreting step;

wherein said providing a plurality of menu items for said menu step comprises creating menu items by:
providing an item name for identifying a menu item;
providing an item type for said menu item;
providing a next menu number for indicating a number of a next menu for display upon selection of said menu item;
providing a pull down keypad number for indicating a plurality of pull down keypads for display upon selection of said menu item;
providing a text string for output on a report;
providing a default string for said menu item; and
repeating said creating a menu item step for each required menu item.

3. The method of claim 2, further comprising checking data in said menu item for validity.

4. The method of claim 3 wherein said providing an item name step comprises providing an item name in alphanumeric English.

5. The method of claim 3 wherein said providing an item type step comprises providing an item type for said item menu, said item type being one of a title, a noun, a pronoun, an adjective, wherein said title is an item which appears as a title on a report, said noun is an item which appears as a title for a type of exam, said pronoun is an item appearing as a subtitle for a type of exam, said adjective is an item which does not appear as a title and does have text associated with it, said text associated with noun, pronoun or adjective items.

6. The method of claim 5 wherein said providing an item type step comprises providing a next menu number for indicating a number of a next menu for display upon selection of said menu item, said next menu number being valid when said item type is said title, said noun, and said pronoun only.

7. The method of claim 6 wherein said providing a pull down keypad step comprises providing a pull down keypad number for indicating a plurality of pull down keypads for display upon selection of said menu item, said pull down keypad number being valid only when said item type is said adjective.

8. The method of claim 6 wherein said step f) comprises generating a written report based on selections from said menu items, data from said pull down keypads, said text strings, and said default strings.

9. The method of claim 3 wherein said providing a text string step comprises providing a text string for output on a report, wherein said text string is a fixed English text capable of having variable data items inserted.

10. In a programmed portable computer system, said system having a first mode for set up and customization and a second mode for collecting information, a method for generating written reports for a user comprising the steps of:

a) entering said first mode for set up and customization;

b) creating menus in said first mode by:
i) selecting a menu title for identifying said menu,
ii) assigning a current menu number for uniquely identifying said menu by said system,
iii) providing a plurality of menu items wherein said plurality of menu items comprises a plurality of programmable menu items which are changeable by the user, and a plurality of fixed menu items which are not changeable by the user, wherein said providing a plurality of menu items comprises creating a menu item by providing an item name for identifying said menu item,
iv) providing an item type for said menu item, said item type being one of a title, a noun, a pronoun, an adjective, wherein said title is an item which appears as a title on a report, said noun is an item which appears as a title for a type of exam, said pronoun is an item appearing as a subtitle for a type of exam, said adjective is an item which does not appear as a title and does have text associated with it, text may be associated with noun, pronoun or adjective type item,
v) providing a next menu number for indicating a number of a next menu for display upon selection of said menu item, said next menu number being valid for said item type is said title, said noun, and said pronoun only,
vi) providing a pull down keypad number for indicating a plurality of pull down keypads for display upon selection of said menu item, said pull down keypad number being valid only if said item type is said adjective,
vii) providing a text string for output on a report,
viii) providing default strings for said menu item,
ix) repeating said creating a menu item step for each required menu item, and
x) repeating said creating a menu step thereby providing a plurality of menus;

c) entering said second mode for collecting information;
d) in said second mode, entering information using said programmed plurality of menus by:
   i) entering demographic and medical information for a patient,
   ii) selecting an exam type, said exam type specifying an exam to be performed,
   iii) in response to said selecting step, displaying selected ones of said programmed plurality of menus,
   iv) entering exam information into said selected ones of said programmed plurality of menus, and
   v) entering additional information by writing on a screen;
e) interpreting said entered information to format a written report based on said entered information; and
f) generating said written report in response to said interpreting step.

11. In a programmed portable computer system, a method for generating medical exam reports based on succinct input from a user comprising the steps of:

selecting a first mode for customizing menus for entering information;

in said first mode, defining a plurality of menus to enter information, said plurality of menus including menus for entering medical history and medical exam information;

in said first mode, selecting an item type for a menus, wherein said item type is a title, noun, pronoun or adjective and selecting a pull down keypad for use with an adjective item type;

selecting a second mode for entering information;

in said second mode, entering medical history information utilizing at least one of said plurality of menus;

in said second mode, entering medical exam information utilizing at least one of said plurality of menus; and generating a report based on said entered information.

\* \* \* \* \*